United States Patent
Abdelhamid et al.

(10) Patent No.: US 12,352,739 B1
(45) Date of Patent: Jul. 8, 2025

(54) METHOD OF HEAVY METAL ION DETECTION USING CHEMOSENSORS

(71) Applicant: IMAM MOHAMMAD IBN SAUD ISLAMIC UNIVERSITY, Riyadh (SA)

(72) Inventors: Hani Nasser Abdelhamid, Riyadh (SA); Faisal Khuwayshan L Algethami, Riyadh (SA); Hussein El-Kashef, Assiut (EG)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 19/052,060

(22) Filed: Feb. 12, 2025

(51) Int. Cl.
*G01N 33/18* (2006.01)
*C07D 277/34* (2006.01)
*G01N 21/64* (2006.01)

(52) U.S. Cl.
CPC ....... *G01N 33/1813* (2013.01); *C07D 277/34* (2013.01); *G01N 21/64* (2013.01)

(58) Field of Classification Search
CPC ... G01N 21/64; G01N 33/1813; C07D 277/34
See application file for complete search history.

(56) References Cited

U.S. PATENT DOCUMENTS

| | | | |
|---|---|---|---|
| 2015/0212059 A1* | 7/2015 | Schechter | G01N 33/1813 436/79 |
| 2021/0172923 A1* | 6/2021 | Kaufman | C07K 16/44 |
| 2024/0352309 A1 | 10/2024 | Zhang | |

FOREIGN PATENT DOCUMENTS

| | | | | |
|---|---|---|---|---|
| CN | 105838355 B | 6/2018 | | |
| CN | 106483111 B | 11/2018 | | |
| CN | 109970730 B | 6/2022 | | |
| CN | 113979968 B | 11/2022 | | |
| CN | 116354901 A | * | 6/2023 | ............ C07D 417/06 |
| CN | 116953040 A | * | 10/2023 | ............. G01N 27/26 |

OTHER PUBLICATIONS

K. Srikanth KUMAR, et al., "Design, synthesis, biological evaluation and molecular docking studies of novel 3-substituted-5-[(indol-3-yl) methylene]-thiazolidine-2, 4-dione derivatives", Heliyon, vol. 4, Issue 9, Sep. 13. 2018, e00807, 26 pages.

* cited by examiner

*Primary Examiner* — Wayne A Langel
(74) *Attorney, Agent, or Firm* — Oblon, McClelland, Maier & Neustadt, L.L.P.

(57) ABSTRACT

A method of detecting a heavy metal ion in an aqueous sample includes contacting a potassium salt of 5-(3,4,5-trimethoxybenzylidene) thiazolidine-2,4-dione ($C_{13}H_{12}KNO_5S$) with the aqueous sample to form a heavy metal complex. The method further includes measuring the fluorescence emission of the aqueous sample to detect the heavy metal complex.

20 Claims, 19 Drawing Sheets

50 →

Contact a potassium salt of 5-(3,4,5-trimethoxybenzylidene)thiazolidine-2,4-dione with the aqueous sample to form a heavy metal complex — 52

↓

Measure the fluorescence emission of the aqueous sample to detect the heavy metal complex — 54

METHOD OF HEAVY METAL ION DETECTION USING CHEMOSENSORS

BACKGROUND

Technical Field

The present disclosure is directed towards a method of detecting a heavy metal ion, and more particularly, relates to the use of potassium salt-based compounds for the detection of heavy metal ions in an aqueous solution.

Description of Related Art

The "background" description provided herein presents the general context of the disclosure. Work of the presently named inventors, to the extent it is described in this background section and aspects of the description which may not otherwise qualify as prior art at the time of filing, are neither expressly nor impliedly admitted as prior art against the present invention.

Industrial discharges, mining waste, landfill leachates, agricultural practices, and urban runoff are primary sources of heavy metal pollution in water. Even at low concentrations, heavy metal ions can be highly toxic to living organisms, causing various health issues. Ingestion of water contaminated with heavy metals can lead to various health problems, including gastrointestinal issues, neurological disorders, reproductive issues, and kidney damage. Thus, water quality monitoring is needed to detect heavy metal contamination.

The detection of heavy metal ions has been achieved using various analytical methods, including electrochemical techniques, high-performance liquid chromatography (HPLC), atomic emission spectrometry, inductively coupled plasma mass spectrometry (ICP-MS), electrophoresis, and ion-selective electrodes. Conventional methods, such as atomic spectrometry, colorimetry, and chromatography, though effective, are often costly, have low sensitivity, and are unsuitable for real-time, simple, and rapid analysis. Compared to conventional methods, fluorescence spectroscopy offers several advantages, such as high sensitivity, increased selectivity, fast analysis time, relatively low cost, suitability for in-situ monitoring, and the ability to detect trace amounts of heavy metals.

Organic compounds have emerged as potential fluorescent chemosensors for fluorescence spectroscopy in heavy metal ion detection due to their tunable structures, high sensitivity, and strong selectivity toward specific analytes. These compounds may interact with metal ions through S-, O-, and N-donor atoms, resulting in measurable changes in fluorescence emission signals. The use of organic compounds as fluorescent chemosensors for heavy metal ion detection presents several challenges, such as limited stability under harsh conditions, potential interference from complex sample matrices, and difficulties in large-scale production. Thus, there exists a need for a stable, sensitive, and selective organic compound for use as a fluorescent chemosensor.

Accordingly, one object of the present disclosure is to provide a method for detecting heavy metal ions utilizing an organic compound as a fluorescent chemosensor.

SUMMARY

In an embodiment, a method of detecting a heavy metal ion in an aqueous sample is described. The method comprises contacting a potassium salt of 5-(3,4,5-trimethoxybenzylidene) thiazolidine-2,4-dione ($C_{13}H_{12}KNO_5S$) with the aqueous sample to form a heavy metal complex. The method further comprises measuring the fluorescence emission of the aqueous sample to detect the heavy metal complex. The heavy metal ion is at least one selected from the group including lead (Pb), cadmium (Cd), copper (Cu), zinc (Zn), mercury (Hg), and nickel (Ni). Furthermore, the aqueous sample has a pH of 1 to 10, and the heavy metal ion is present in the aqueous sample in an amount of at least 0.1 micromolar (µM).

In some embodiments, the potassium salt of 5-(3,4,5-trimethoxybenzylidene) thiazolidine-2,4-dione has a band gap of 2 to 3.5 electron volt (eV).

In some embodiments, the heavy metal ion is at least one selected from the group including lead and cadmium.

In some embodiments, the potassium salt of 5-(3,4,5-trimethoxybenzylidene) thiazolidine-2,4-dione has a band gap of 2.7 to 2.9 eV.

In some embodiments, the method comprises obtaining a thiazolidine-2,4-dione by reacting chloroacetic acid ($C_2H_3ClO_2$) with a thiourea ($CH_4N_2S$), condensing the thiazolidine-2,4-dione with a tri-substituted benzaldehyde in the presence of a catalyst, to obtain 5-(3,4,5-trimethoxybenzylidene) thiazolidine-2,4-dione, and further reacting the 5-(3,4,5-trimethoxybenzylidene) thiazolidine-2,4-dione with potassium hydroxide (KOH) to form the potassium salt of 5-(3,4,5-trimethoxybenzylidene) thiazolidine-2,4-dione.

In some embodiments, the method comprises reacting chloroacetic acid with thiourea in a molar ratio of 1:3 to 3:1.

In some embodiments, the potassium salt of 5-(3,4,5-trimethoxybenzylidene) thiazolidine-2,4-dione is characterized by a diffuse reflectance spectroscopy (DRS) pattern comprising a broad absorption band at 300 to 500 nanometer (nm).

In some embodiments, the method comprises condensing the thiazolidine-2,4-dione with the tri-substituted benzaldehyde in a molar ratio of 1:2 to 2:1.

In some embodiments, the catalyst comprises acetic acid ($C_2H_4O_2$) and at least one amine catalyst selected from the group consisting of piperidine ($C_5H_{11}N$), 4-methylpiperidine ($C_6H_{13}N$), piperazine ($C_4H_{10}N_2$), pyrrolidine ($C_4H_9N$), and hexamethylenediamine ($C_6H_{13}N$).

In some embodiments, the catalyst comprises piperidine and acetic acid.

In some embodiments, the fluorescence emission of the potassium salt of 5-(3,4,5-trimethoxybenzylidene) thiazolidine-2,4-dione is 5 to 35 absorbance unit (a.u.) at a wavelength of 400 nm to 500 nm when 0.1 to 1 M of lead is present in the aqueous sample.

In some embodiments, the fluorescence emission of the potassium salt of 5-(3,4,5-trimethoxybenzylidene) thiazolidine-2,4-dione is 20 to 35 a.u. at a wavelength of 460 nm to 500 nm when 0.1 to 1 µM of lead is present in the aqueous sample.

In some embodiments, the potassium salt of 5-(3,4,5-trimethoxybenzylidene) thiazolidine-2,4-dione is a direct band gap material.

In some embodiments, the fluorescence emission of the potassium salt of 5-(3,4,5-trimethoxybenzylidene) thiazolidine-2,4-dione potassium salt is 10 to 30 a.u. at a wavelength of 400 to 600 nm at a pH of 1 to 3.

In some embodiments, the fluorescence emission of the potassium salt of 5-(3,4,5-trimethoxybenzylidene) thiazolidine-2,4-dione is 5 to 30 a.u. at a wavelength of 400 to 600 nm when 0.1 to 1 µM of cadmium is present in the aqueous sample.

In some embodiments, the fluorescence emission of the potassium salt of 5-(3,4,5-trimethoxybenzylidene) thiazolidine-2,4-dione is 15 to 30 a.u. at a wavelength of 460 to 500 nm when 0.1 to 1 μM of cadmium is present in the aqueous sample.

In some embodiments, the aqueous sample has a pH of 1 to 8.

In some embodiments, the method comprises contacting the potassium salt of 5-(3,4,5-trimethoxybenzylidene) thiazolidine-2,4-dione to the aqueous sample for 20 minutes (min).

In some embodiments, the aqueous sample has a pH of 1 to 3.

In some embodiments, the potassium salt of 5-(3,4,5-trimethoxybenzylidene) thiazolidine-2,4-dione has a melting point of 170 to 260° C.

The general description of the illustrative embodiments and the following detailed description are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
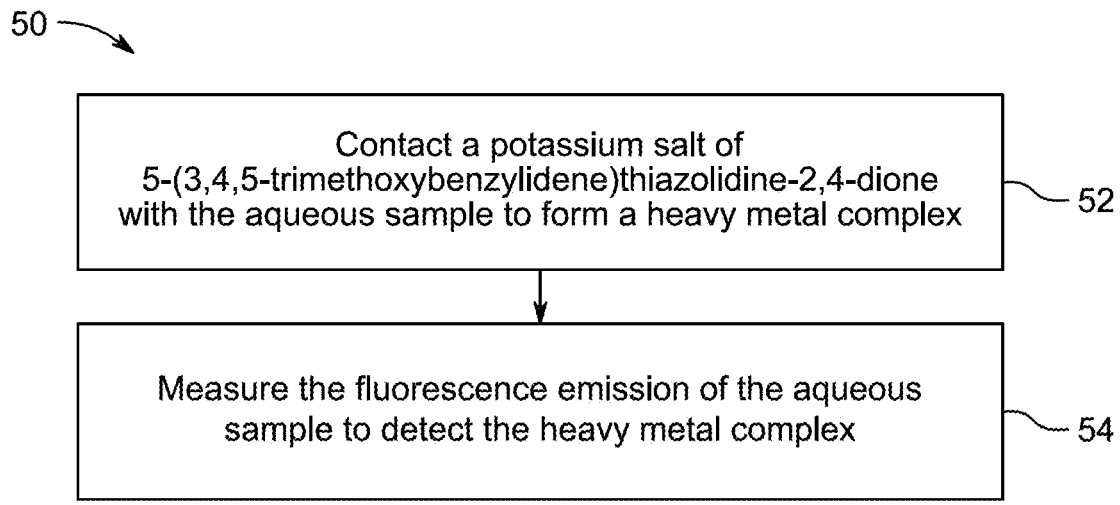
FIG. 1A is a flowchart depicting a method detecting a heavy metal ion in an aqueous sample, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values between.

As used herein, the term 'heavy metal ion' refers to a positively charged particle (ion) of metal or metalloid with a high density. Examples of heavy metal ion such as lead ($Pb^{2+}$), cadmium ($Cd^{2+}$), mercury ($Hg^{2+}$), and arsenic ($As^{3+}$). Heavy metal ions are non-biodegradable and can be harmful to humans and the environment at low concentrations. They can cause a variety of health issues, including cardiovascular disease, cancer, and neurological disorders.

As used herein, the term 'direct band gap material' refers to a semiconductor where the minimum energy in the conduction band and the maximum energy in the valence band occur at the same momentum, allowing electrons to transition directly between bands and emit photons with high efficiency. Direct band gap materials may be useful in applications like LEDs and lasers.

As used herein, the term 'catalyst' refers to a substance that speeds up a chemical reaction, or lowers the temperature or pressure needed to start one, without itself being consumed during the reaction. Catalysts may be categorized as homogeneous catalysts (existing in the same phase as the reactants) and heterogeneous catalysts (existing in a different phase than the reactants), with examples like enzymes (biocatalysts) falling under the homogeneous category and solid metals, like platinum, often used as heterogeneous catalysts in processes like catalytic converters.

As used herein, the term 'fluorescence emission' refers to the process by which a fluorescent molecule emits light after exposure to excitation light. Fluorescence emission is a type of photoluminescence, which is the emission of light by a substance that has absorbed light or other electromagnetic radiation. The process occurs when a molecule absorbs energy from radiation or particles, such as X-rays or electrons, exciting the molecule's atoms. The excited molecule's energy decays or decreases, emitting light energy. The emitted light is usually visible light, but the color depends on the chemical composition of the molecule. The emission intensity increases when the excitation intensity increases, with the emitted light usually having a longer wavelength than the excitation light.

As used herein, the term 'Knoevenagel condensation' refers to a chemical reaction where an aldehyde or ketone reacts with a compound containing an active methylene group (a carbon between two electron-withdrawing groups) in the presence of a base catalyst, resulting in the formation of an α,β-unsaturated carbonyl compound through a carbon-carbon bond formation and subsequent dehydration step. The Knoevenagel condensation reaction is a modified Aldol Condensation reaction with a nucleophilic addition between the aldehyde or ketone, and an active hydrogen compound in the presence of a basic catalyst, resulting in C—C bond formation As used herein, the term 'absorption band' refers to a range of wavelengths, frequencies, or energies in the electromagnetic spectrum that a substance absorbs. Absorption bands are unique to each substance and by analyzing them, a material's composition, structure, and physical properties may be determined.

As used herein, the term 'diffuse reflectance spectra (DRS)' pattern refers to a graph that shows the amount of light reflected from a sample at different wavelengths. It is created using a technique called diffuse reflectance spectroscopy (DRS), which measures the amount of light reflected from a sample in the ultraviolet to visible range. The reflected light is a combination of light reflected from the surface and light reflected internally, which is modified by the sample's absorption bands. The difference in signal between the sample and a reference material is used to create the diffuse reflectance spectrum.

Aspects of the present disclosure are directed to synthesizing a water-soluble potassium salt of 1,3-thiazolidine-2, 4-diones, making it suitable for detecting heavy metal ions in aqueous solutions. The potassium salt exhibits a selective fluorescence response to lead and cadmium ions, with fluorescence intensity varying depending on pH. The detection method comprises introducing the potassium salt into an aqueous solution and measuring fluorescence to detect and quantify heavy metal ions, with a sensitivity limit of 0.1 µM. The method of the present disclosure operates without organic solvents, making it eco-friendly for field use. Additionally, this chemosensor is scalable, cost-effective, and can be integrated into commercial test kits for environmental water quality testing.

FIG. 1A illustrates a flow chart of a method 50 of detecting a heavy metal ion in an aqueous sample. Heavy metal ions are toxic metallic elements like arsenic, chromium, cobalt, antimony, lead, cadmium, copper, zinc, mercury, nickel, and thallium. Heavy metal ions may be dissolved in water sources, posing a significant threat to human health and aquatic ecosystems due to their potential for bioaccumulation and harmful effects on human organs like the liver, kidneys, and nervous system. Heavy metal ions may enter water sources through industrial waste, mining activities, agricultural runoff, and urban wastewater. In some embodiments, the heavy metal ion is least one selected from the group consisting of lead, cadmium, copper, zinc, mercury, and nickel. In a preferred embodiment, the heavy metal ion is at least one selected from the group consisting of lead and cadmium. In an embodiment, the concentration of the heavy metal ion present in the aqueous sample may be at least 0.001 µM, preferably at least 0.002 µM, preferably at least 0.003 µM, preferably at least 0.004 µM, preferably at least 0.005 µM, preferably at least 0.006 µM, preferably at least 0.007 µM, preferably at least 0.008 UM, preferably at least 0.009 UM, preferably at least 0.01 µM, preferably at least 0.02 µM, preferably at least 0.03 µM, preferably at least 0.04 µM, preferably at least 0.05 µM, preferably at least 0.06 µM, preferably at least 0.07 µM, preferably at least 0.08 µM, preferably at least 0.09 preferably at least 0.01 µM, preferably at least 0.02 µM, preferably at least 0.03 µM, preferably at least 0.04 µM, most preferably at least 0.1 µM.

Suitable examples of the aqueous sample include, but are not limited to, tap water, drinking water, surface water, such as river water and lake water, underground water, such as well water and spring water, drinking water, waste water, or seawater. The aqueous sample has a pH of 1 to 10, preferably 1 to 9, preferably 1 to 8, preferably 1 to 7, preferably 1 to 6, preferably 1 to 6, preferably 1 to 5, preferably 1 to 4, most preferably 1 to 3.

The order in which the method 50 is described is not intended to be construed as a limitation, and any number of the described method steps can be combined in any order to implement the method 50. Additionally, individual steps may be removed or skipped from the method 50 without departing from the spirit and scope of the present disclosure.

At step 52, the method 50 comprises contacting a potassium salt of 5-(3,4,5-trimethoxybenzylidene) thiazolidine-2, 4-dione with the aqueous sample to form a heavy metal complex. In some embodiments, the method of contacting the potassium salt of 5-(3,4,5-trimethoxybenzylidene) thiazolidine-2,4-dione with the aqueous sample is carried for at least 1 minute, preferably at least 2 min, preferably at least 3 min, preferably at least 4 min, preferably at least 5 min, preferably at least 6 min, preferably at least 7 min, preferably at least 8 min, preferably at least 9 min, preferably at least 10 min, preferably at least 11 min, preferably at least 12 min, preferably at least 13 min, preferably at least 14 min, preferably at least 15 min, preferably at least 16 min, preferably at least 17 min, preferably at least 18 min, preferably at least 19 min, most preferably at least 20 min.

In some embodiments, 5-(3,4,5-trimethoxybenzylidene) thiazolidine-2,4-dione and the potassium salt thereof has a melting point of 170 to 260° C. In a specific embodiment, 5-(3,4,5-trimethoxybenzylidene) thiazolidine-2,4-dione has a melting point of 170 to 200° C., preferably 171 to 199° C., preferably 172 to 198° C., preferably 173 to 197° C., preferably 174 to 196° C., preferably 175 to 195° C., preferably 176 to 194° C., preferably 177 to 193° C., preferably 178 to 192° C., preferably 179 to 191° C., preferably 180 to 190° C., preferably 181 to 189° C., preferably 182 to 188° C., preferably 183 to 187° C., preferably 184 to 187° C., most preferably 185 to 187° C. In a specific embodiment, the potassium salt of 5-(3,4,5-trimethoxybenzylidene) thiazolidine-2,4-dione has a melting point of 220 to 260° C., preferably 221 to 259° C., preferably 222 to 258° C., preferably 223 to 257° C., preferably 224 to 256° C., preferably 225 to 255° C., preferably 226 to 255° C., preferably 227 to 255° C., preferably 228 to 255° C., preferably 229 to 255° C., preferably 230 to 255° C., preferably 231 to 255° C., preferably 232 to 255° C., preferably 233 to 255° C., preferably 234 to 255° C., preferably 235 to 255° C., preferably 236 to 255° C., preferably 237 to 255° C., preferably 238 to 255° C., preferably 239 to 255° C., preferably 240 to 255° C., preferably 241 to 255° C., preferably 242 to 255° C., preferably 243 to 255° C., preferably 244 to 255° C., preferably 245 to 255° C., preferably 246 to 255° C., preferably 247 to 255° C., preferably 248 to 255° C., preferably 249 to 255° C., most preferably 250 to 255° C.

Salts, preferably those containing calcium, potassium, or sodium, are utilized in heavy metal ion removal from water sources through a process called chemical precipitation, where the salt acts as a chelating agent, binding to the heavy metal ions to form an insoluble precipitate that can be easily separated from the water source through filtration or sedimentation. In some embodiments, a potassium salt may bind a heavy metal ion by forming ionic bonds with the negatively charged functional groups on the salt molecule, trapping the positively charged heavy metal ions and creating a precipitate, effectively removing them from the water source. This process may be facilitated by the potassium ion's ability to stabilize the resulting complex due to its relatively large positive charge, allowing for multiple binding sites with the heavy metal ion.

In some embodiments, the potassium salt of 5-(3,4,5-trimethoxybenzylidene) thiazolidine-2,4-dione is a direct band gap material. Direct band materials are materials in which the minimum energy state in the conduction band and the maximum energy state in the valence band occur at the same k-vector (momentum) in the Brillouin zone, allowing for efficient absorption and emission of photons with energies close to the band gap, resulting in strong fluorescence emission as compared to indirect band gap materials where momentum conservation is a significant factor limiting light emission. Due to the alignment of energy states, electrons in a direct band gap material can easily transition between the valence and conduction bands when excited by a photon, leading to high probability of light emission upon relaxation. Direct band gap materials often exhibit relatively narrow emission peaks in their fluorescence spectra, as the transition between the bands is well defined. In an embodiment, 5-(3,4,5-trimethoxybenzylidene) thiazolidine-2,4-dione and the potassium salt thereof has a band gap of 2 to 3.5 eV, preferably 2.1 to 3.4 eV, preferably 2.2 to 3.3 eV, preferably 2.3 to 3.2 eV, preferably 2.4 to 3.1 eV, preferably 2.5 to 3.0 eV, preferably 2.6 to 2.9 eV, most preferably 2.7 to 2.9 eV. A band gap of a compound refers to the energy difference between the valence band (filled with electrons) and the conduction band (empty states) in a material, representing the amount of energy needed to excite an electron from its normal state to a state where it can freely conduct electricity. A compound with a smaller band gap generally indicates a greater potential to adsorb and remove heavy metal ions effectively. When a compound with a smaller band gap comes into contact with heavy metal ions, the electrons from the valence band can readily transition to the metal ions, forming a chemical bond and effectively removing the metal from the solution.

A diffuse reflectance spectrum measures the intensity of light reflected from a sample at different wavelengths, where the light is scattered in various directions due to the sample's structure and composition. In some embodiments, the potassium salt of 5-(3,4,5-trimethoxybenzylidene) thiazolidine-2,4-dione is characterized by a diffuse reflectance spectra (DRS) pattern including a broad absorption band at 300 to 500 nm, preferably 500 nm, preferably 400 nm.

At step 54, the method 50 comprises measuring the fluorescence emission of the aqueous sample to detect the heavy metal complex. The heavy metal complex formation results in a change in the fluorescence emission of the aqueous sample. Changes in fluorescence intensity, wavelength shifts, or quenching indicate the presence and concentration of the heavy metal ion. In one embodiment, the fluorescence emission of the potassium salt of 5-(3,4,5-trimethoxybenzylidene) thiazolidine-2,4-dione illustrates a quantifiable response to the presence of lead and cadmium ions in aqueous samples. This response varies in intensity and spectral shift depending on the concentration of the metal ions and the pH of the solution. In an embodiment, the fluorescence emission of the potassium salt of 5-(3,4,5-trimethoxybenzylidene) thiazolidine-2,4-dione is 5 to 35 a.u. at a wavelength of 400 to 500 nm when 0.1 to 1 µM of lead is present in the aqueous sample. In one embodiment, the fluorescence emission of the potassium salt of 5-(3,4,5-trimethoxybenzylidene) thiazolidine-2,4-dione is 20 to 35 a.u. at a wavelength of 460 to 500 nm when 0.1 to 1 µM of lead is present in the aqueous sample. In an embodiment, the fluorescence emission of the potassium salt of 5-(3,4,5-trimethoxybenzylidene) thiazolidine-2,4-dione potassium salt is 10 to 30 a.u. at a wavelength of 400 to 600 nm at a pH of 1 to 3. In one embodiment, the fluorescence emission of the potassium salt of 5-(3,4,5-trimethoxybenzylidene) thiazolidine-2,4-dione is 5 to 30 a.u. at a wavelength of 400 to 600 nm when 0.1 to 1 µM of cadmium is present in the aqueous sample. In one embodiment, the fluorescence emission of the potassium salt of 5-(3,4,5-trimethoxybenzylidene) thiazolidine-2,4-dione is 15 to 30 a.u. at a wavelength of 460 to 500 nm when 0.1 to 1 µM of cadmium is present in the aqueous sample.

Figure 1B:
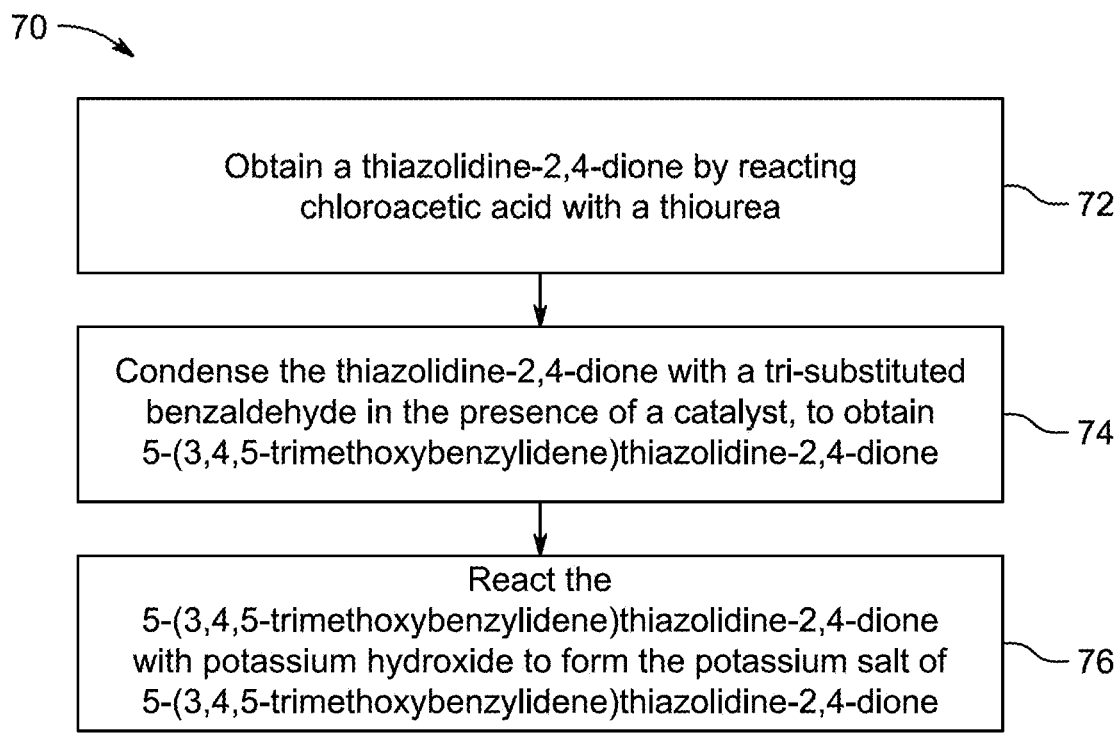
FIG. 1B is a flowchart depicting a method of preparing a potassium salt of 5-(3,4,5-trimethoxybenzylidene) thiazolidine-2,4-dione (compound 2), according to certain embodiments.

FIG. 1B illustrates a flow chart of a method 70 for preparing the potassium salt of 5-(3,4,5-trimethoxybenzylidene) thiazolidine-2,4-dione. The order in which the method 70 is described is not intended to be construed as a limitation, and any number of the described method steps can be combined in any order to implement the method 70. Additionally, individual steps may be removed or skipped from the method 70 without departing from the spirit and scope of the present disclosure.

At step 72, the method 70 comprises obtaining a thiazolidine-2,4-dione by reacting chloroacetic acid with a thiourea. The molar ratio of chloroacetic acid to thiourea is in a ratio of 1:3 to 3:1, preferably 1:2.5 to 2.5:1, preferably 1:2 to 2:1, preferably 1:1.5 to 1.5:1, most preferably 1:1 chloroacetic acid to thiourea. In some embodiments, the chloroacetic acid is reacted with thiourea in an acidic medium. The acidic medium in the synthesis of thiazolidine-2,4-dione may facilitate the reaction by promoting nucleophilic attack, enhancing reactant solubility, stabilizing intermediates, and helping to control side reactions, thus improving reaction efficiency and yield. In some embodiments, the acidic medium comprises at least one selected from the group consisting of hydrochloric acid, nitric acid, sulfuric acid, phosphoric acid, carbonic acid, citric acid, hydrobromic acid, hydroiodic acid, perchloric acid, and acetic acid. In a preferred embodiment, the acidic medium comprises hydrochloric acid.

At step 74, the method 70 comprises condensing the thiazolidine-2,4-dione with a tri-substituted benzaldehyde in the presence of a catalyst, to obtain 5-(3,4,5-trimethoxybenzylidene) thiazolidine-2,4-dione. In some embodiments, the molar ratio of thiazolidine-2,4-dione to the tri-substituted benzaldehyde in a molar ratio of 1:4 to 4:1, preferably 1:3.5 to 3.5:1, preferably 1:3 to 3:1 preferably 1:2.5 to 2.5:1, preferably 1:2 to 2:1, preferably 1:1.5 to 1.5:1, most preferably 1:1 thiazolidine-2,4-dione to tri-substituted benzaldehyde. In an embodiment, the catalyst comprises acetic acid and at least one amine catalyst selected from the group consisting of triethylamine, diethylamine, morpholine, N,N-dimethylbenzylamine, and 1,4-diazabicyclo[2.2.2]octane (DBN), piperidine, 4-methylpiperidine, piperazine, pyrrolidine, and hexamethylenediamine. In some embodiments, the amine catalyst is at least one selected from the group consisting of piperidine, 4-methylpiperidine, piperazine, pyrrolidine, and hexamethyleneimine. In a preferred embodiment, the catalyst comprises piperidine and acetic acid.

At step 76, the method 70 comprises reacting the 5-(3,4,5-trimethoxybenzylidene) thiazolidine-2,4-dione with potassium hydroxide to form the potassium salt of 5-(3,4,5-trimethoxybenzylidene) thiazolidine-2,4-dione. The potassium hydroxide deprotonates the 5-(3,4,5-trimethoxybenzylidene) thiazolidine-2,4-dione, converting it into its corresponding potassium salt and enhancing the ability of the compound to complex with metal ions.

EXAMPLES

The following examples demonstrate a method of detecting a heavy metal ion in an aqueous sample. The examples are provided solely for illustration and are not to be construed as limitations of the present disclosure, as many variations thereof are possible without departing from the spirit and scope of the present disclosure.

Example 1: Materials and Methods

According to the present disclosure, cadmium nitrate tetrahydrate ($Cd(NO_3)_2 \cdot 4H_2O$) and lead nitrate ($Pb(NO_3)_2$) were purchased from Sigma Aldrich, Germany. A 1 millimolar (mM) solution was prepared as a sample in tap water. All chemical reagents were used without further purification. All melting points were determined using a Stuart instrument, (SMP3). Infrared spectra were acquired by a Nicolet iS10 Fourier transform infrared (FT-IR) spectrometer employing the KBr method. The proton nuclear magnetic resonance ($^1H$ NMR) spectra were acquired on a Bruker Avance 300 spectrometer from the Faculty of Pharmacy, University of Lille, France, functioning at 300 megahertz (MHz) for proton nuclear magnetic resonance ($^1H$ NMR) and 75 MHz for carbon-13 nuclear magnetic resonance ($^{13}C$ NMR). The chemical shifts for $^1H$ NMR and $^{13}C$ NMR were measured in parts per million (ppm) and referenced to the residual proton peaks in deuterated solvents, including deuterated chloroform ($CDCl_3$) at 7.26 ppm for $^1H$ and 76.90 ppm for $^{13}C$, and deuterated dimethyl sulfoxide (DMSO-d6) at 2.50 ppm for $^1H$ and 39.70 ppm for $^{13}C$. Multiplicities were denoted as s (singlet), d (doublet), t (triplet), q (quartet), and m (multiplet). Coupling constants (J) were expressed in Hertz (Hz). Mass spectra were obtained using liquid chromatography-mass spectrometry (LC-MS), Waters Alliance Micromass ZQ 2000. LC-MS analysis was performed using a Waters XBridge C18 column with a 5 micrometer (μm) particle size and dimensions of 50 millimeters (mm)×4.6 mm. A gradient elution method was employed, starting with 98% water ($H_2O$)/formate buffer with a concentration of 5 millimolar (mM) and a pH adjusted to 3.8 and progressing to 100% acetonitrile ($CH_3CN$)/formate buffer a concentration of 5 mM and a pH adjusted to 3.8 over 4 minutes at a flow rate of 2 milliliters per minute (mL/min), followed by a return to the initial conditions within 1 minute. Elemental analyses for carbon (C), hydrogen (H), and nitrogen (N) were performed using a Perkin Elmer 240 C Micro analyzer, with results closely matching theoretical values within +0.4%, which means the actual value may be 0.4% higher or lower than the reported value.

Example 2: Synthesis of Organic Molecules for Compound 1 and Compound 2

For synthesizing an aqueous solution of thiazolidine-2,4-dione, around 0.5 moles of chloroacetic acid and 0.5 moles of thiourea were dissolved in 50 mL of water in a 250 mL round-bottom flask. The resultant mixture was agitated for 15 minutes and subsequently cooled, resulting in the formation of a white precipitate. 30 mL of concentrated hydrochloric acid (HCl) was gradually added to the mixture using a dropping funnel. Furthermore, the precipitate was washed with three portions of 50 mL of water (3×50 mL) to remove any impurities or residual reactants, and dried. The solution was then refluxed for 10 hours at a temperature of 100° C. Furthermore, the solution was purified via recrystallization using ethyl alcohol ($C_2H_{60}$). The obtained compound was subsequently utilized as a precursor for synthesizing compounds 1 and 2.

Example 3: Synthesis of 5-(3,4,5-Trimethoxybenzylidene) thiazolidine-2,4-dione ($C_{13}H_{13}NO_5S$) (Compound 1)

Figure 1C:
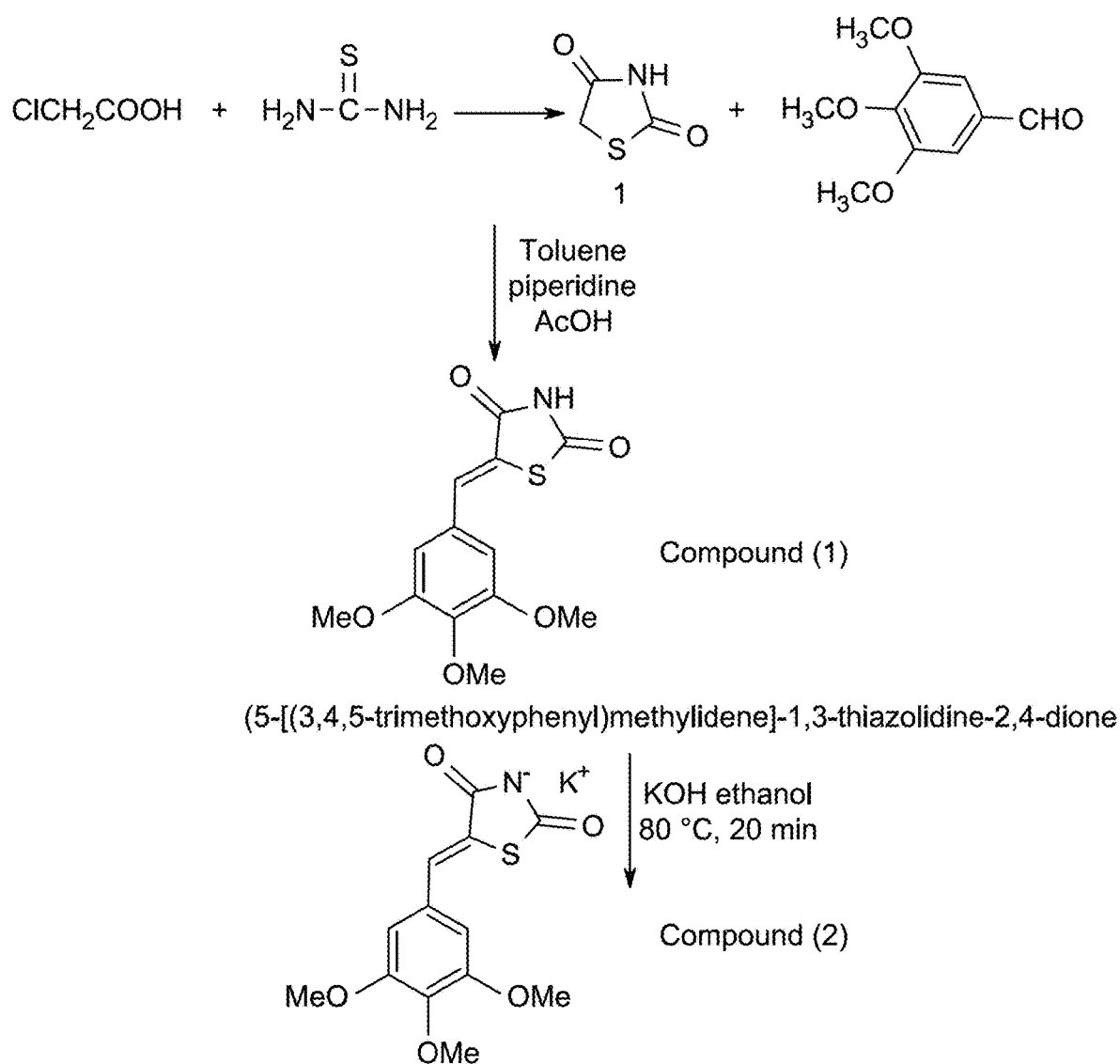
FIG. 1C is a synthesis scheme for the preparation of 5-(3,4,5-Trimethoxybenzylidene) thiazolidine-2,4-dione ($C_{13}H_{13}NO_5S$) (compound 1) and compound 2, according to certain embodiments.

The synthesis of compound 1 was performed as shown in FIG. 1C. Thiazolidine-2,4-dione was synthesized by reacting chloroacetic acid ($CCl_2HCOOH$) with thiourea ($NH_2CSNH_2$) in acidic conditions. The obtained thiazolidine-2,4-dione then underwent a Knoevenagel condensation with 3,4,5-trimethoxy benzaldehyde ($C_8H_8O_4$), catalyzed by piperidine ($C_5H_{11}N$) and acetic acid ($CH_3COOH$), resulting in the formation of 5-(3,4,5-trimethoxybenzylidene) thiazolidine-2,4-dione. The synthesis of the mixture comprises 20 millimoles (mmol) of equimolar thiazolidine-2,4-dione and 20 mmol of 3,4,5-trimethoxy benzaldehyde in 50 mL of anhydrous toluene ($C_7H_8$). The solution was refluxed with a few drops of acetic acid ($CH_3COOH$) and piperidine ($C_5H_{11}NH$) in a flask equipped with a Dean-Stark apparatus. The reaction mixture was refluxed for 15 hours. Furthermore, after the reaction mixture cooled to room temperature, the resulting solid product was separated from the reaction mixture through filtration. The solid was thoroughly washed with a small volume of toluene ($C_7H_8$) to remove impurities or residual reactants. The washed product was then dried under appropriate conditions, forming a fine powder. The purified product was recrystallized from cyclohexane ($C_6H_{12}$), yielding pale yellow crystals weighing 5.49 grams (g), corresponding to a yield of 93%, with a melting point ranging from 185° C. to 187° C. IR (wavenumber, $cm^{-1}$): 3176 $cm^{-1}$ (N—H), 3020 $cm^{-1}$ (aromatic C—H), 2950-2992 $cm^{-1}$ (aliphatic C—H), 1748 $cm^{-1}$ (C═O), 1698 $cm^{-1}$ (C═O), 1606 $cm^{-1}$, 1576 $cm^{-1}$, 1506 $cm^{-1}$, and 1451 $cm^{-1}$ (aromatic C═C). $^1H$ NMR (300 MHz, DMSO d6): δ 3.72 (s, 3H, —$OCH_3$), 3.82 (s, 6H, 2-$OCH_3$), 6.91 (s, 2H, Ar—H), 7.25 (s, 1H, —CH═), 12.59 (s, 1H, NH); $^{13}C$ NMR (75 MHz, DMSO d6): δ 56.4 (2-$OCH_3$), 60.6 (—$OCH_3$), 107.9 (2 CH), 122.9 (C), 128.9 (C), 132.5 (C), 139.8 (CH), 153.6 (2C), 167.7 (C═O), 168.3 (C═O). Mass spectrometry in negative mode shows a mass-to-charge ratio (m/z) of 294.3 corresponding to [M-H]. Further, analysis conducted for $C_{13}H_{13}NO_5S$ (molecular weight: 295.31) indicated the theoretical composition of 52.87% for carbon (C), 4.44% for hydrogen (H), 4.74% for nitrogen (N), and identified the composition of C, H, N was 52.90%, 4.19%, and 4.66%, respectively.

Example 4: Synthesis of the Potassium Salt of 5-(3,4,5-Trimethoxybenzylidene) Thiazolidine-2,4-Dione ($C_{13}H_{12}KNO_5S$) (Compound 2)

Potassium 5-(3,4,5-trimethoxybenzylidene) thiazolidine-2,4-dione salt, compound 2, was produced by reacting compound 1 with potassium hydroxide in ethanol. For the synthesis of compound 2, approximately 1.1 mmol of potassium hydroxide (KOH) solution in 3 mL of ethanol ($C_2H_5OH$) was added to a heated solution of compound 1, which contained 0.3 grams, equivalent to 1 millimoles of compound 1. The reaction mixture was further heated under stirring at about 80° C. for 20 minutes. The resulting precipitate was carefully filtered to separate it from the reaction mixture. After filtration, the precipitate was thoroughly washed with ethanol ($C_2H_5OH$) to remove residual impurities or unreacted materials. The washed precipitate was then dried under appropriate conditions to obtain the required solid product. The final yield was 0.28 g, corresponding to a yield of 83%, and decomposition at melting point 250-255° C. IR (v, cm$^{-1}$): 3026 cm$^{-1}$ (aromatic CH), 2998 cm$^{-1}$ (aliphatic CH), 2940 cm$^{-1}$ (aliphatic CH), 2835 cm$^{-1}$ (aliphatic CH), 1732 cm$^{-1}$ (C=O), 1682 cm$^{-1}$ (C=O), 1607 cm$^{-1}$, 1573 cm$^{-1}$, 1500 cm$^{-1}$, 1448 cm$^{-1}$, and 1430 cm$^{-1}$ (aromatic C=C). $^1$H NMR (300 MHz, DMSO-d6) δ (ppm): 3.68 (s, 3H, —OCH$_3$), 3.80 (s, 6H, 2-OCH$_3$), 6.86 (s, 2H, ArH), 7.25 (s, 1H, —CH=). $^{13}$C-NMR (75 MHz, DMSO d6) δ (ppm): 56.2 (2-OCH$_3$), 60.5 (—OCH$_3$), 106.8 (2C—H), 122.8 (C), 132.0 (C), 136.0 (C), 137.7 (CH), 153.3 (2 C), 176.0 (C=O), 183.3 (C=O). Mass spectrometry (ESI-) m/z 294.3 [M–H]$^-$. Analysis conducted for $C_{13}H_{12}KNO_5S$ (molecular weight: 333.40) indicated the following theoretical composition: carbon (C) 46.83%, hydrogen (H) 3.63%, and nitrogen (N) 4.20%. The observed elemental composition was 46.58% C, 3.50% H, 4.00% N.

Example 5: Characterization of Compound 1 and Compound 2 with Fluorescence, UV-Vis Spectroscopy, and DRS In the present disclosure, stock solutions of compounds 1 and 2 were prepared by dissolving them in 10 mL of water to achieve a 1 mg/mL concentration. Metal salt solutions were prepared in tap water as a real sample with a concentration of 1 mM. The solutions were used as stock solutions. Fluorescence measurements were carried out using a 3 mL solution, which included 100 μL of the probe solution. To achieve final concentrations of 0.1 μM to 1 μM, 1 L to 1000 μL of the metal solution was added from the stock solution. The final volume of the mixture was adjusted with water. All solutions were allowed to stand for 20 minutes before measurements were taken. The pH effect on the solution was studied over a range of 1-10, using hydrochloric acid (HCl) and 1 molar (M) sodium hydroxide (NaOH) for pH adjustments. The excitation wavelength was set at 350 nanometers (nm), with a slit size of 20 nm. UV-Vis spectroscopy for the liquid solutions was measured using a UV-Vis spectrophotometer, Agilent Cary 60, Eclipse. Fluorescence spectroscopy measurements were recorded using an Agilent Cary Eclipse spectrofluorometer (Agilent, Eclipse, USA). Diffuse reflectance spectroscopy (DRS) for solid-state compounds was recorded using Evolution 220 (Thermo Fisher Scientific, USA). The optical bandgap (Eg) was determined using the Tauc's plot and the transformed Kubelka-Munk function according to Equation 1

$$(\alpha h v)n = A(hv - Eg) \quad \text{Equation 1}$$

where: A, h, v, α, n, and Eg were absorption coefficients, Planck's constant, light frequency, constant, n=2, and band-gap energy, respectively. The energy in electron volt (eV) was calculated from the wavelength (nm) obtained from UV-Vis spectra using Equation 2, $$E \text{ (eV)} = 1240/\lambda \quad \text{Equation 2}$$

where λ represents the wavelength in nm.

Figure 2A:
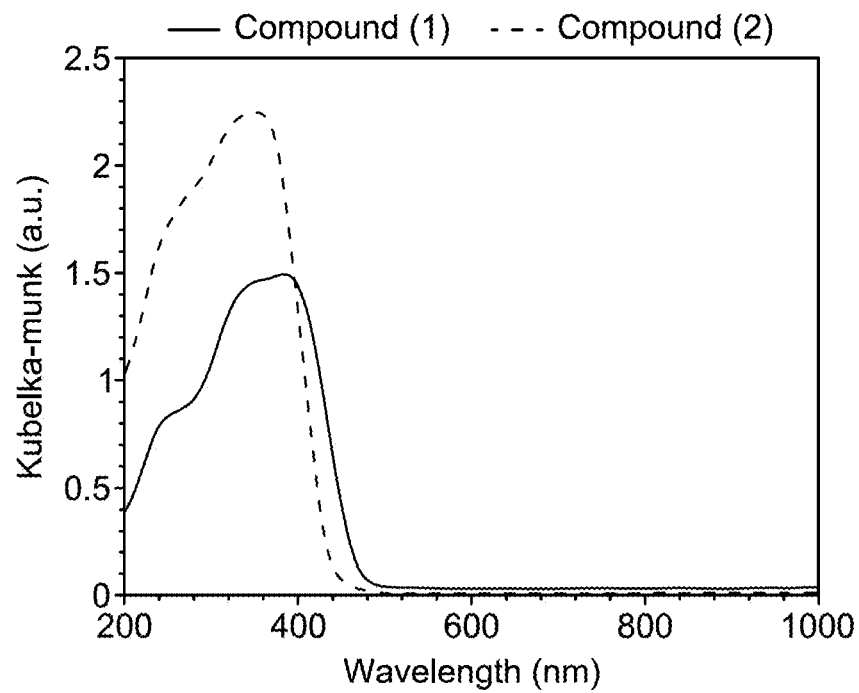
FIG. 2A shows a diffuse reflectance spectroscopy (DRS) for compound 1 and compound 2, according to certain embodiments.

The optical properties of the synthesized compounds 1 and 2 were evaluated using DRS, as shown in FIG. 2A. Both compounds displayed distinctive absorption bands in the UV-visible spectrum. Compound 1 exhibited a distinct absorption band centered at 400 nm, whereas compound 2 showed a broader absorption band with a peak at approximately 500 nm. Compound 1 exhibited more absorption intensity than compound 2, as evidenced by the high Kubelka-Munk values. The detected absorption bands may be ascribed to electronic transitions within the molecular configurations of the compounds. The electronic transitions probably entail the excitation of electrons from ground-state molecular orbitals to elevated-energy excited states. The existence of chromophoric groups, including conjugated π-electron systems, in the molecular structures of substances may affect the absorption characteristics of molecules. The precise characteristics of these chromophore group may influence the location and strength of the absorption bands.

Figure 2B:
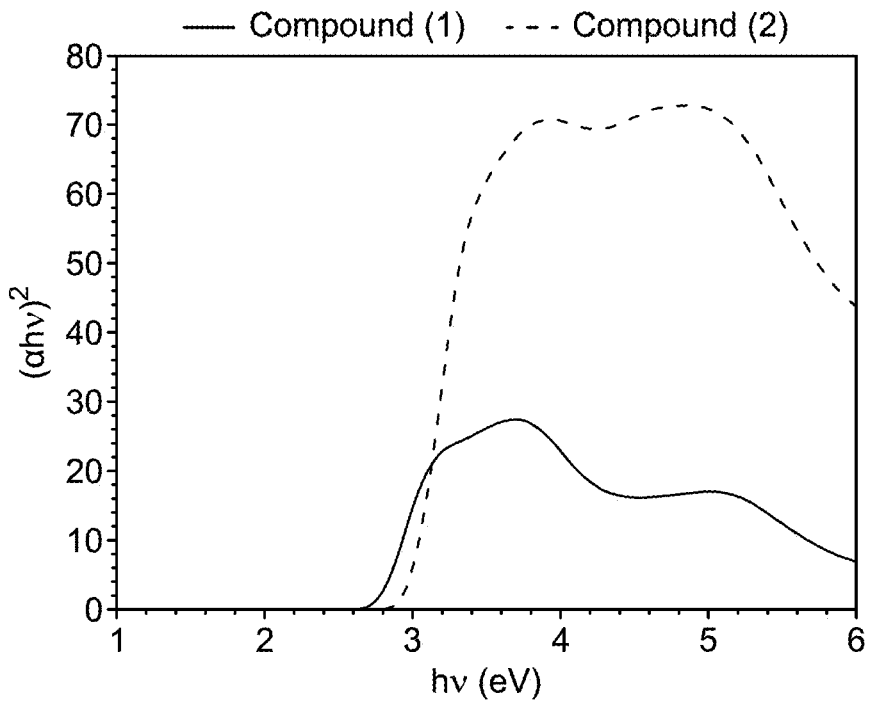
FIG. 2B shows a Tauc plot for compound 1 and compound 2, according to certain embodiments.

The Tauc's plot illustrated an effective method for ascertaining the bandgap energy of materials, shown in FIG. 2B. By graphing the product of the absorption coefficient (a) and photon energy (hv) raised to the power of 1/n against photon energy, the bandgap energy may be determined from the x-axis intercept of the linear segment of the curve. The bandgap energy may be determined from the intersection of the linear segment of the Tauc's plot with the x-axis. Band gap for compound 1 and compound 2 were 2.7 eV and 2.9 eV, respectively. Compound 1 exhibited a greater bandgap energy than compound 2. The configuration of Tauc's plot may elucidate the characteristics of electronic transitions. An abrupt rise in the absorption coefficient near the band edge often signifies a direct bandgap material, whereas a gradual rise implies an indirect bandgap material.

Figure 1D:
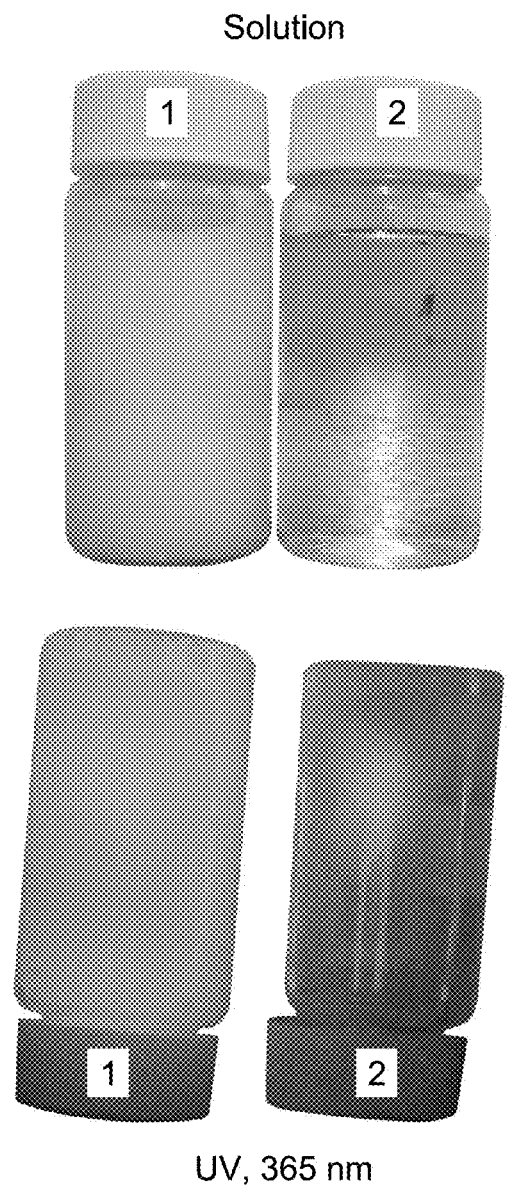
FIG. 1D is a pictorial image of solution of compound 1 and compound 2 without UV light and with UV light, respectively, according to certain embodiments.

The chemical structure of the synthesized molecules, i.e., compound 1 and compound 2, revealed the presence of several heteroatom sites that may interact with metal ions through S—, O—, and N-donor atoms, generating changes in the optical properties of these compounds. Consequently, compound 1 and compound 2 were applied as probes for analyzing heavy metal ions in aqueous solution. The aqueous solution of compounds 1 and 2 using the same concentration, shown in FIG. 1D. Compound 1 was dispersed in water, while compound 2 was dissolved in water, forming a clear solution. Under a UV lamp with a 365 nm intensity, compound 1 emitted a blue emission, as shown in FIG. 1D. On the other side, the water-soluble compound, compound 2, was a non-fluorescent probe.

The effect of pH on the fluorescence emission for compounds 1 and 2 was shown in FIG. 3. The fluorescence spectra and intensity graphs presented significant insights into the pH-dependent characteristics of compounds 1 and 2. The fluorescence spectra for compound 1 at varying pH levels, as shown in FIG. 3A. A slight red-shift in the emission maxima was detected when the pH increased from 1 to 10. The significant observance was notable for the energy level of the excited state of the fluorophore diminished as pH increased. The fluorescence intensity initially showed no dramatic change in the acidic pH ranging from 1-4, as shown in FIG. 3B. Above pH 5, the emission signal decreased with increased pH, and the graphic corroborated the trend identified in the spectra, as shown in FIG. 3B. The fluorescence emission intensity for compound 1 was constant at around 1-4, followed by a decline. The pH-dependent behavior of compound 1 indicated the existence of acid-base equilibria involving the fluorophore. The fluorophore may be protonated at a reduced pH, displaying an elevated energy excited state. As the pH increases, deprotonation transpires, resulting in a less energy-excited state and a red-shifted emission. The reduction in intensity at elevated pH may have resulted from several sources, including photoinduced electron transfer (PET) mechanisms or alterations in the fluorophore's structure.

Figure 3A:
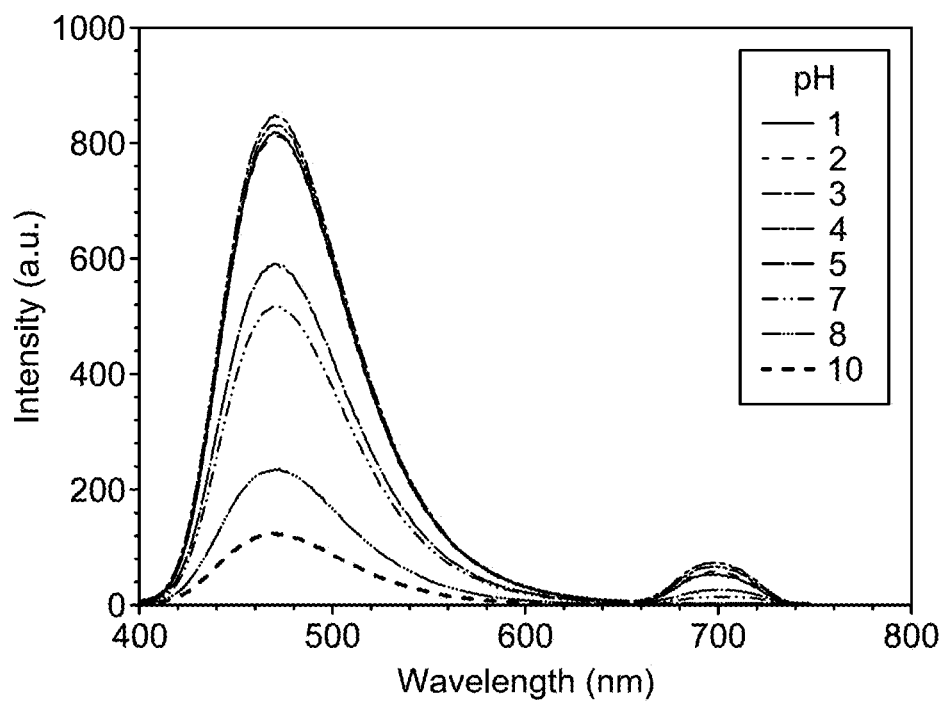
FIG. 3A and FIG. 3B show an effect of pH on the fluorescence emission of compound 1, according to certain embodiments.
Figure 3B:
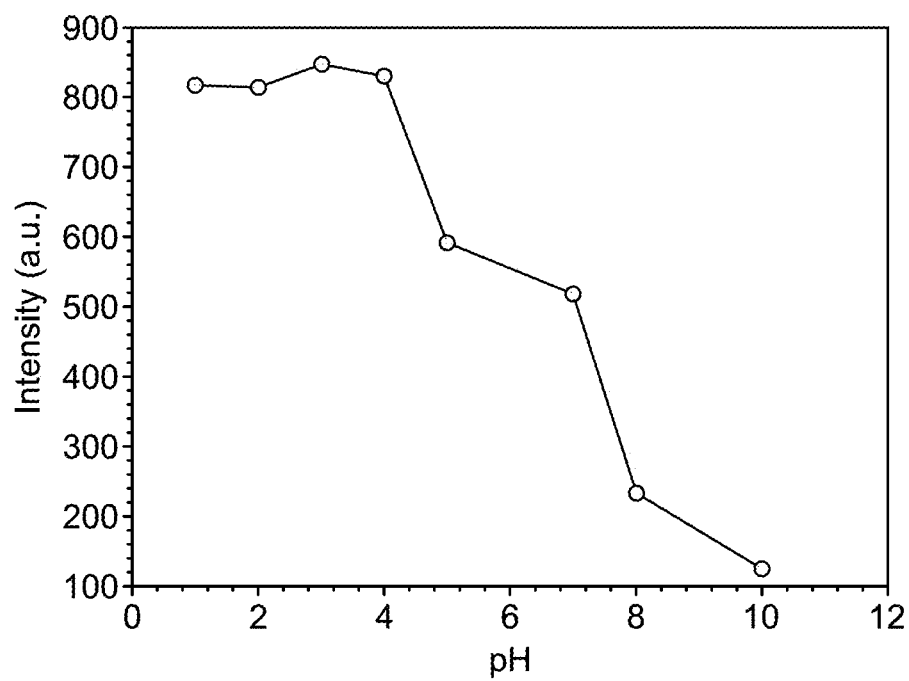
Figure 3C:
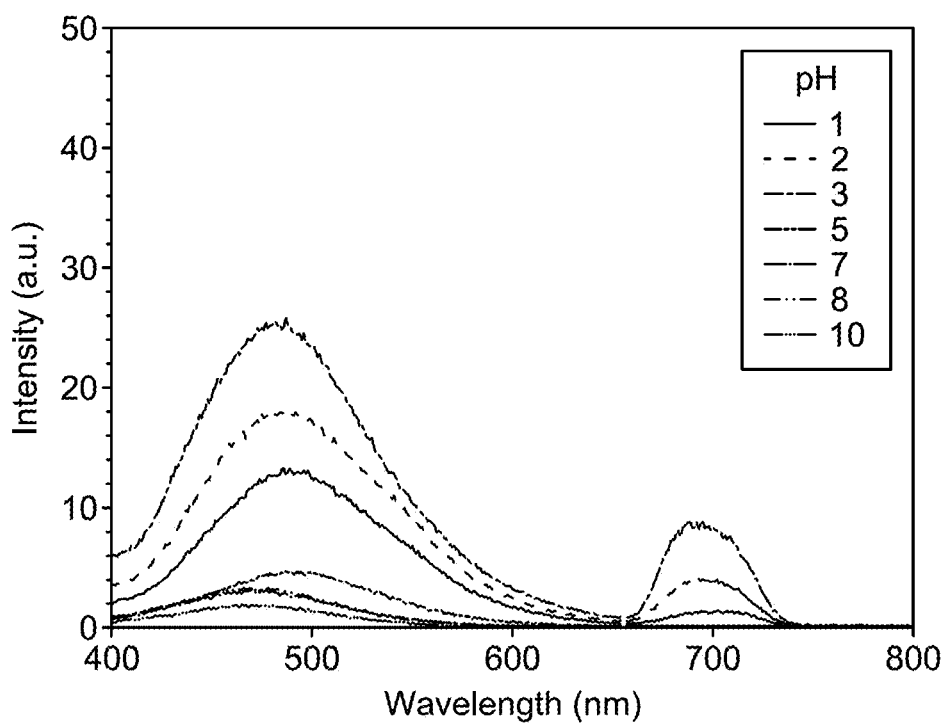
FIG. 3C and FIG. 3D show an effect of pH on the fluorescence emission of compound 2, according to certain embodiments.
Figure 3D:
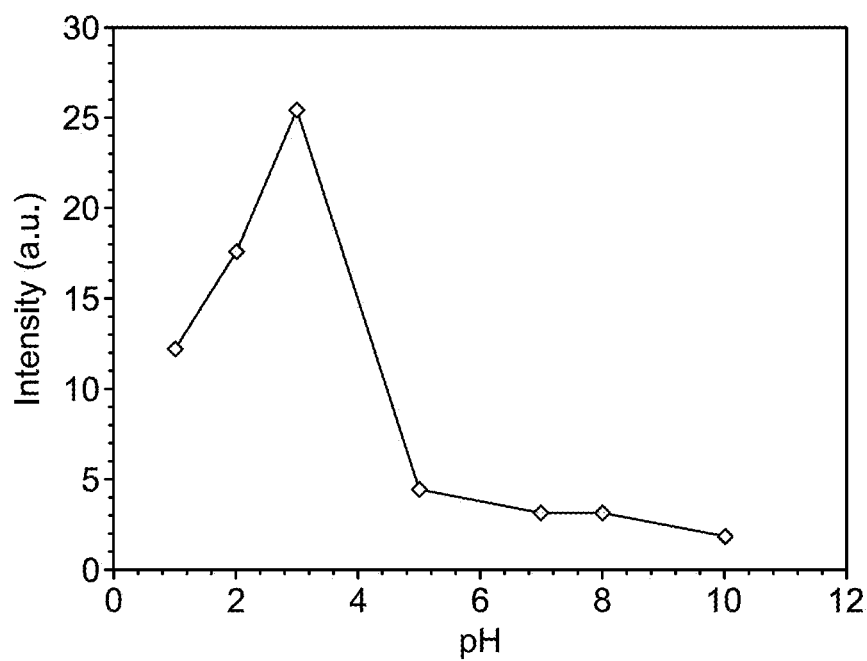

Compound 2 displayed different properties than compound 1 at different pH values, as shown FIG. 3C-3D. The fluorescence intensity escalated with rising pH, peaking at pH 8-9. The graph demonstrated a progressive rise in intensity as pH increased, aligning with the spectral data. The pH-dependent characteristics of compound 2 indicated a distinct acid-base equilibrium mechanism relative to compound 1. The red-shift in the emission maximum signified that deprotonation transpired in compound 2; its impact on the excited state energy level was small. The increase in the emission intensity with pH (1-3) may have resulted from the emergence of a more fluorescent protonated species or the inhibition of non-radiative decay mechanisms. The soluble salt of compound 2 transformed into an insoluble form, similar to compound 1, displaying emission as shown in FIG. 1D. The pH-dependent fluorescence characteristics of compounds 1 and 2 were attributed to acid-base equilibria and their effect on the electronic structure of the fluorophores. These results could be applied in pH sensing, biological imaging, and other areas requiring pH-responsive fluorescent probes.

Figure 4A:
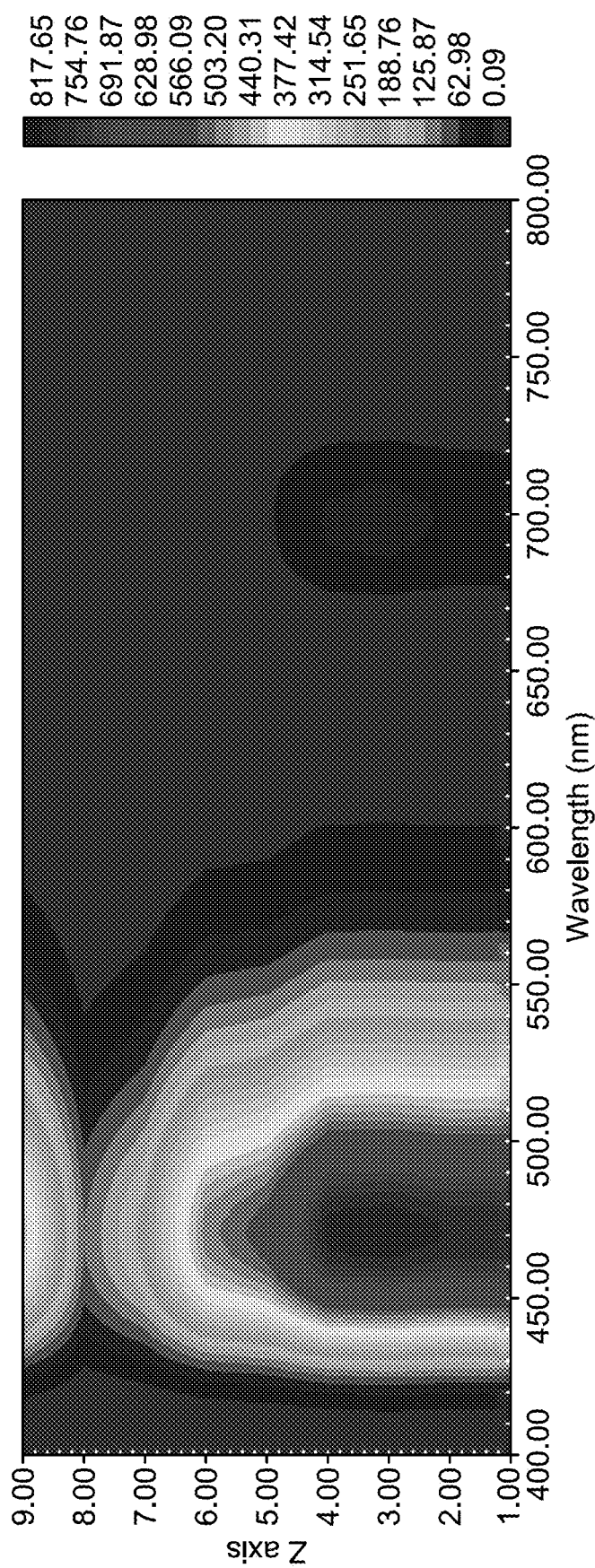
FIG. 4A shows a 2D fluorescence emission of compound 1 at different pH, according to certain embodiments.
Figure 4B:
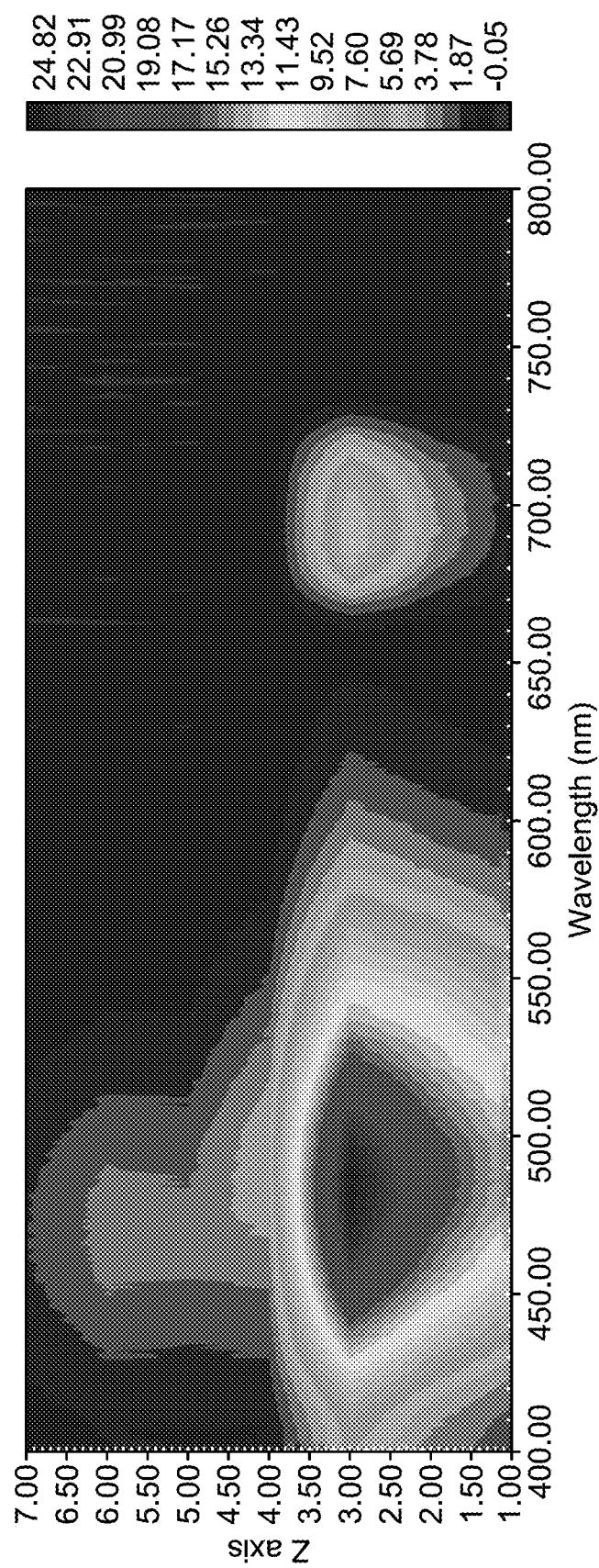
FIG. 4B shows a 2D fluorescence emission of compound 2 at different pH, according to certain embodiments.

The 2D fluorescence spectra of compound 1 demonstrated notable alterations with differing pH levels. As the pH increased, the emission band shifted to longer wavelengths, signifying a bathochromic change. The bathochromic change indicated that the compound experienced a structural alteration or a protonation/deprotonation reaction when the pH increased. The strength of the emission band fluctuated with pH levels, as shown in FIG. 4A-4B. At lower pH, the intensity was comparatively mild, however, it escalates at elevated pH levels. The result may indicate an elevated fluorescence quantum yield or alterations in the molecular environment. Similar to compound 1, compound 2 demonstrated a small pH-dependent shift in emission. However, the extent of the transition was less significant. The emission band intensity of compound 2 remained rather stable over the pH spectrum, indicating that compound 2 molecule exhibited lower sensitivity to pH variations than compound 1. The pH-induced alterations in the emission spectra of both compounds may be ascribed to the protonation or deprotonation of functional groups within the molecules. The modified electronic configuration and, subsequently, the emission properties i.e., wavelength and intensity. As shown in FIGS. 4A-4B, variations in pH prompted conformational alterations in molecules, influencing the electronic interaction among chromophores and resulting in shifts in the emission spectra Compounds 1 and 2 were investigated for detecting heavy metal in tap water as a real sample. Tap water was spiked with toxic heavy metal ions, $Pb^{2+}$ and $Cd^{2+}$ ions, as shown in FIG. 5A-5D. The fluorescence emission spectra demonstrated the reaction of compounds 1 and 2 to $Cd^{2+}$ and $Pb^{2+}$ ions, as shown in FIG. 5A-5D. The spectra compared with and without heavy metal ions helped deduce the possible interactions and the effects of interactions on the compounds' fluorescence characteristics. The incorporation of metal ions resulted in a reduction of fluorescence intensity in both molecules. Heavy metal ions e.g., $Cd^{2+}$ and $Pb^{2+}$, caused fluorescence quenching and enhancement for compounds 1 and 2, as shown in FIG. 5A-5D. The emission spectra displayed variations in the emission maxima, signifying alterations in the energy levels of the excited states for compounds 1 and 2 upon interaction with the heavy metal ions.

Figure 5A:
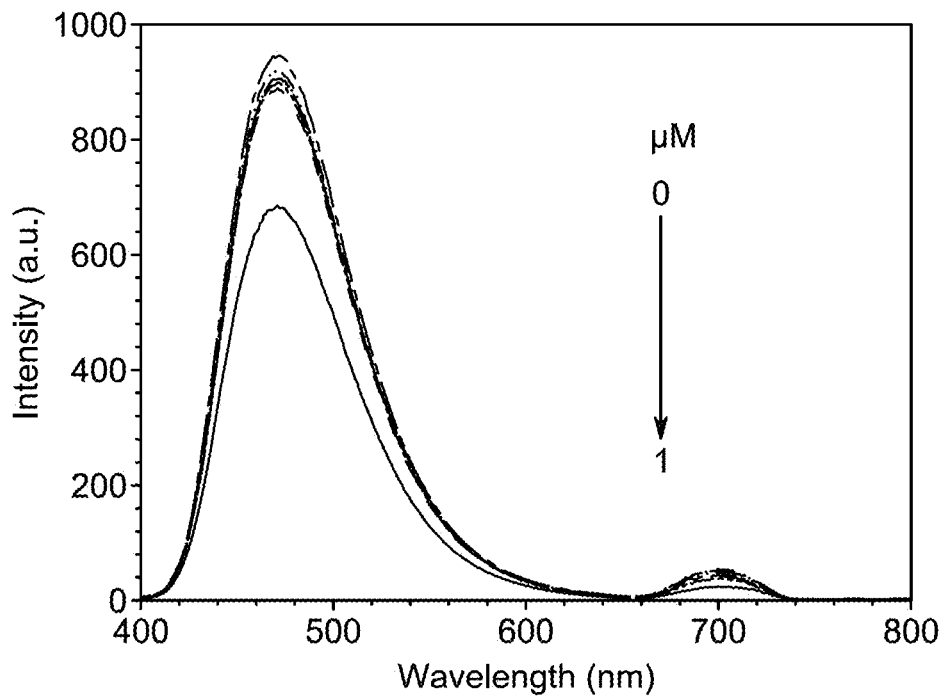
FIG. 5A shows fluorescence emission spectra for compound 1 in the presence of $Cd^{2+}$ ions, according to certain embodiments.
Figure 5B:
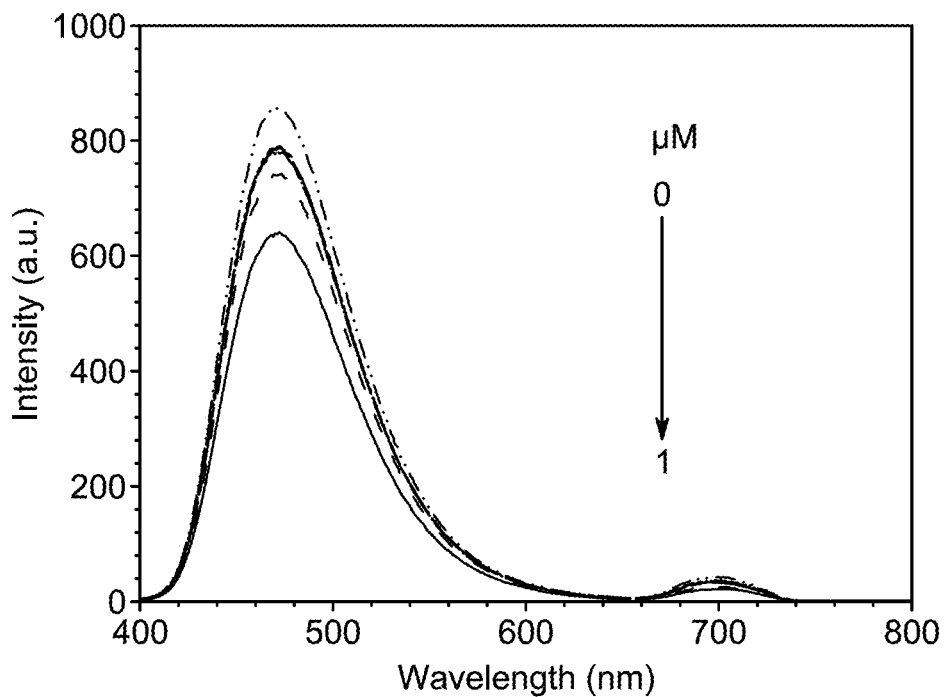
FIG. 5B shows fluorescence emission spectra for compound 1 in the presence of $Pb^{2+}$ ions, according to certain embodiments.
Figure 5C:
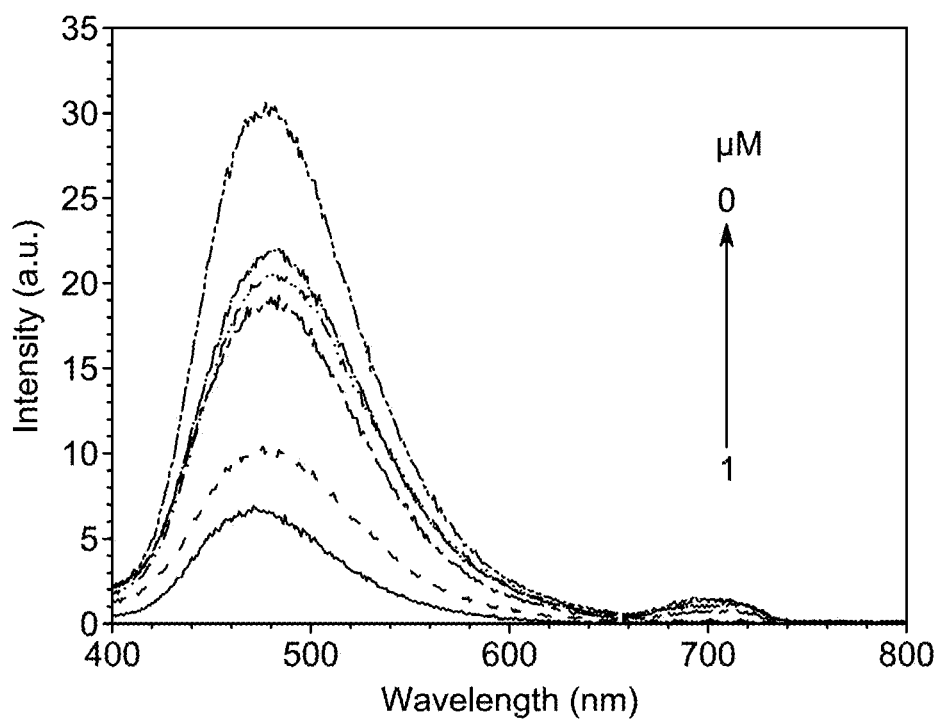
FIG. 5C shows fluorescence emission spectra for compound 2 in the presence of $Cd^{2+}$ ions, according to certain embodiments.
Figure 5D:
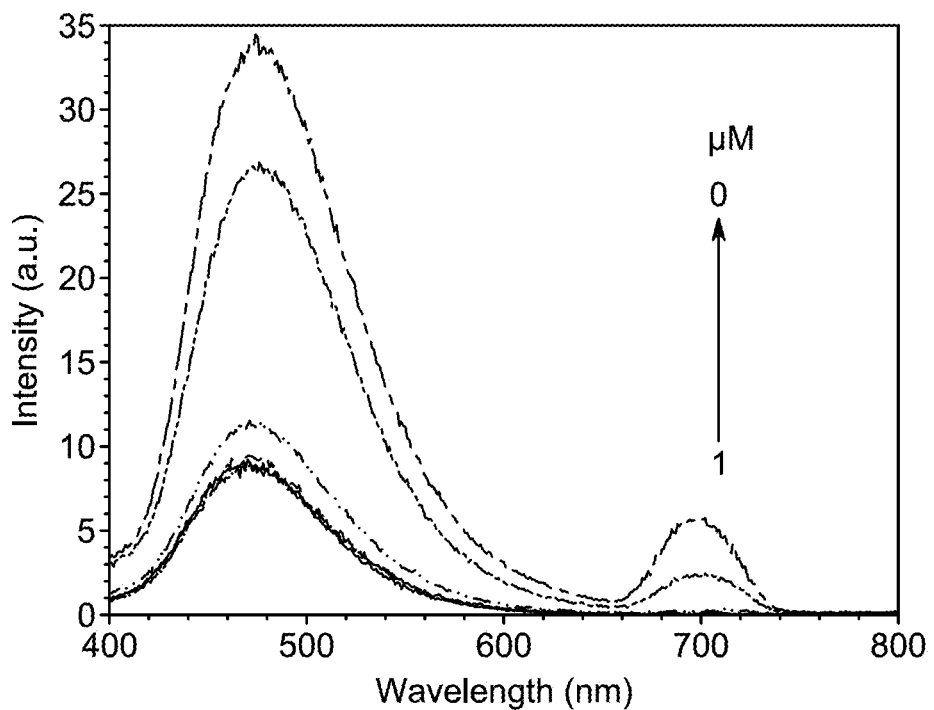
FIG. 5D shows fluorescence emission spectra for compound 2 in the presence of $Pb^{2+}$ ions, according to certain embodiments.

The metal ions created complexes with the fluorophores, i.e., compounds 1 and 2, which reduced the fluorescence intensity of compound 1 without notable alterations in the emission spectrum, as shown in FIG. 5A-5B. Metal ions engaged with the excited state of the fluorophore of compound 1, resulted in non-radiative energy transfer and subsequent deactivation. On the other side, the metal complexation with compound 2 leads to large particles offering emission enhancement, as shown in FIG. 5C-5D.

Figure 6A:
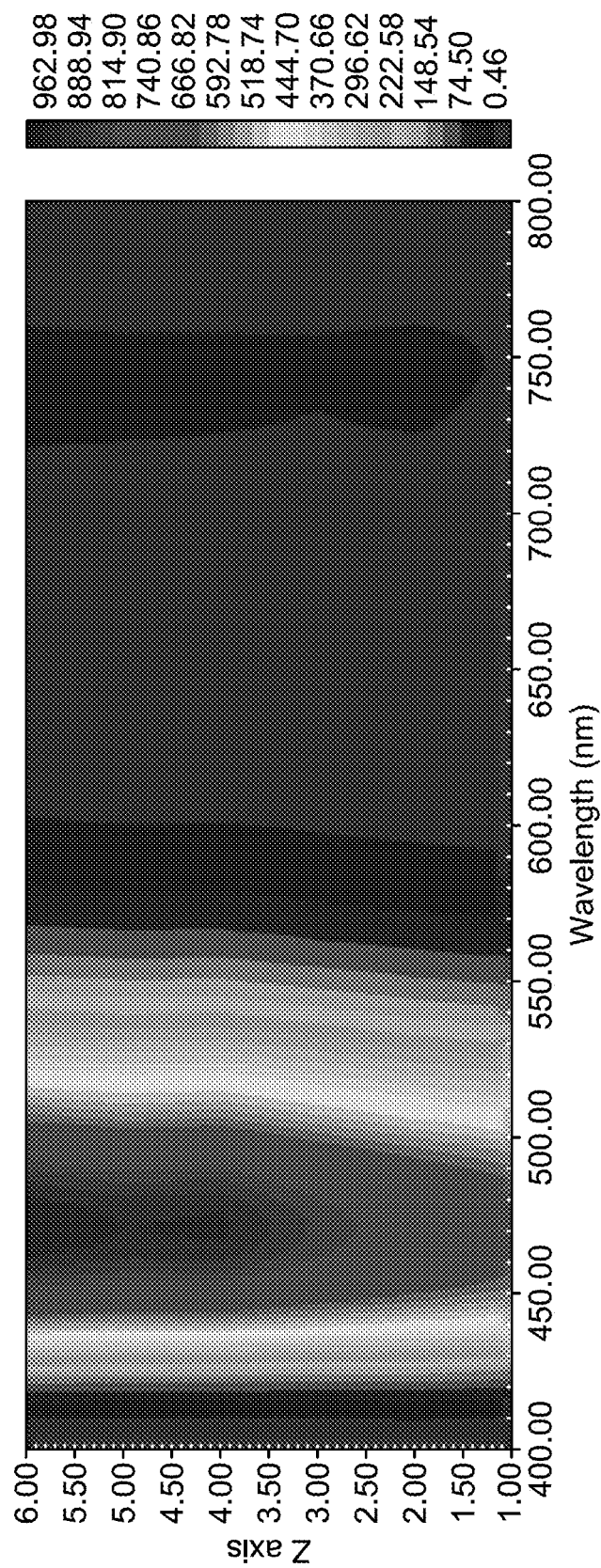
FIG. 6A is a 2D Contour plot for compound 1 in the presence of $Cd^{2+}$ ions, according to certain embodiments.
Figure 6B:
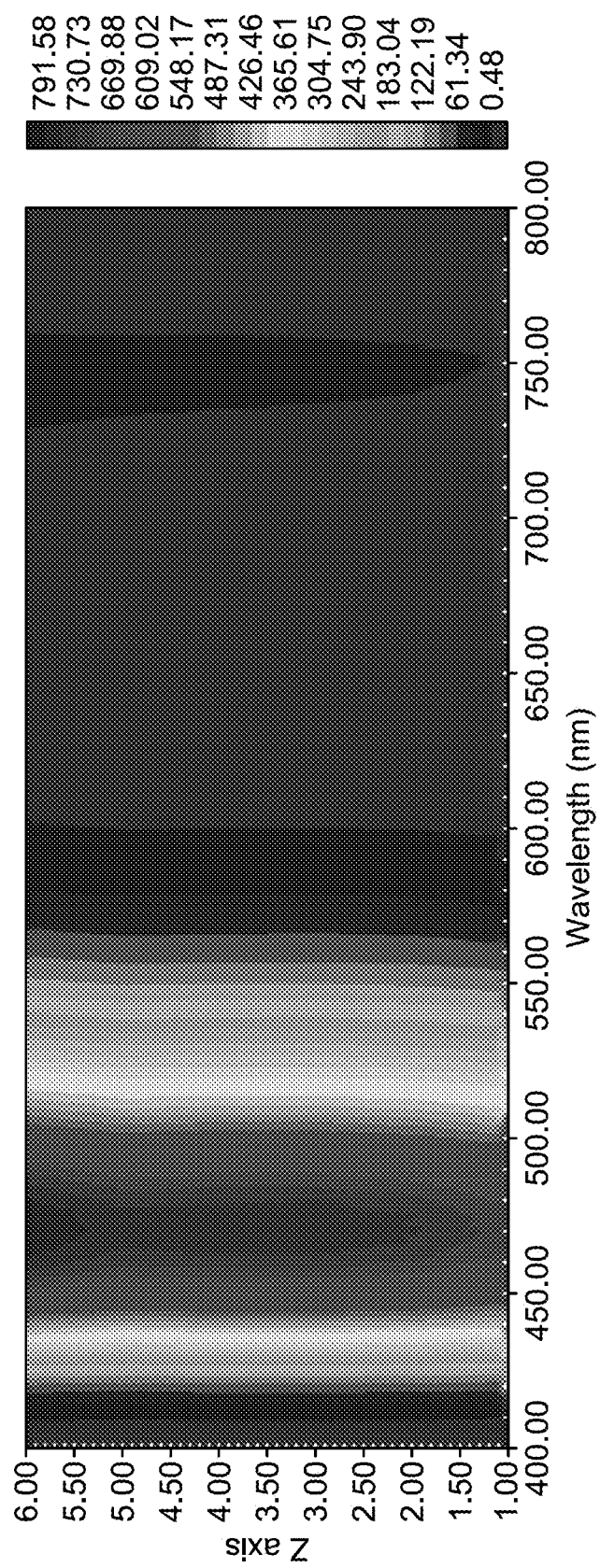
FIG. 6B is a 2D Contour plot for compound 1 in the presence of $Pb^{2+}$ ions, according to certain embodiments.
Figure 6C:
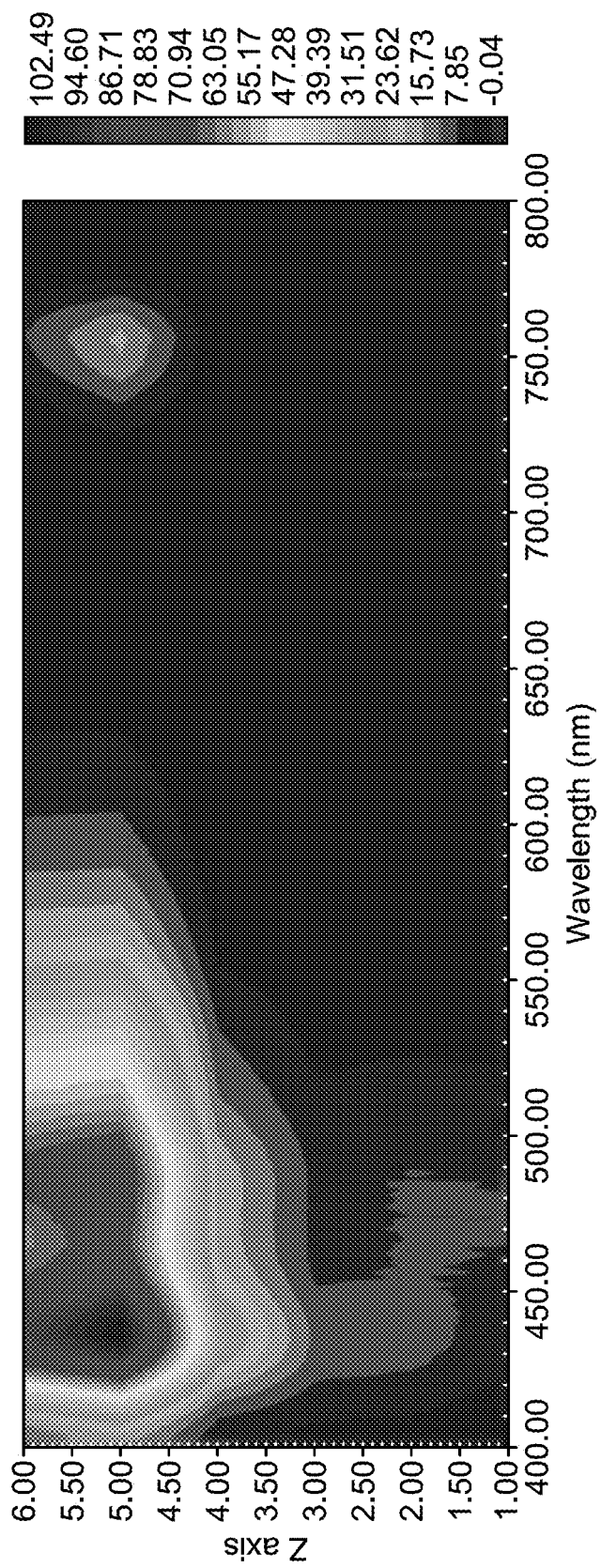
FIG. 6C is a 2D Contour plot for compound 2 in the presence of $Cd^{2+}$ ions, according to certain embodiments.
Figure 6D:
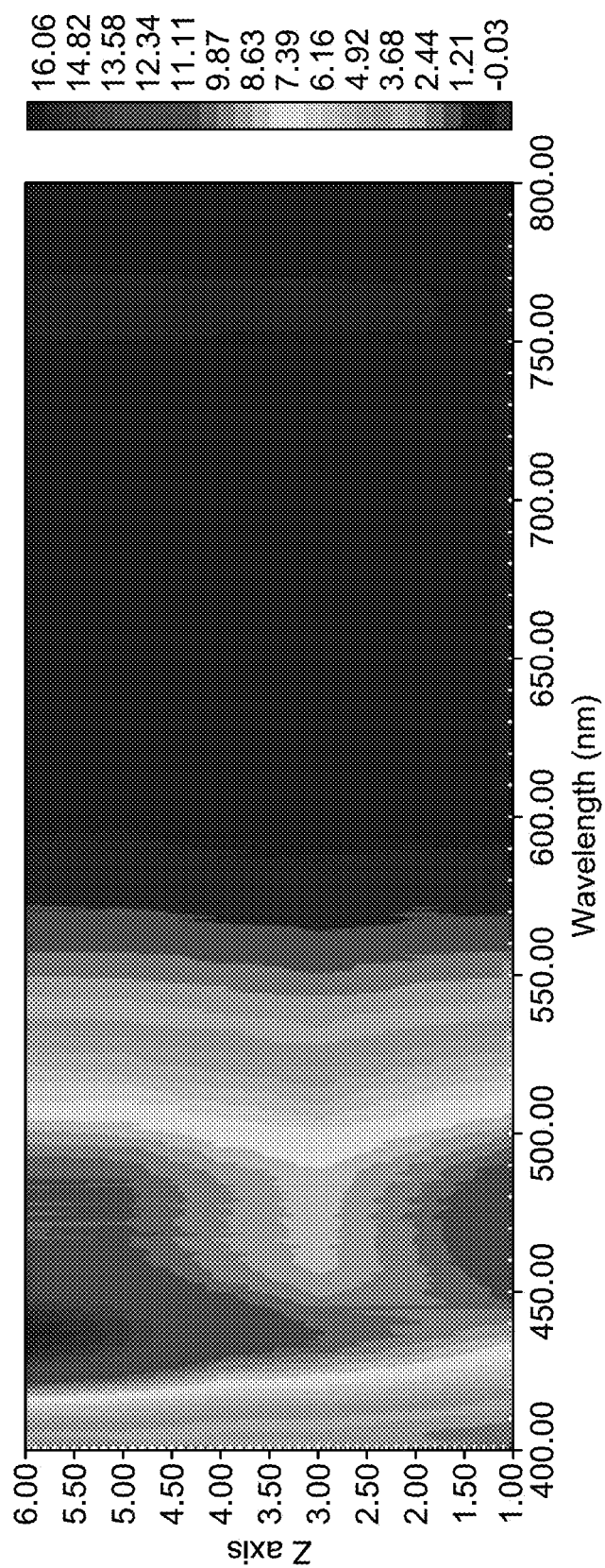
FIG. 6D is a 2D Contour plot for compound 2 in the presence of $Pb^{2+}$ ions, according to certain embodiments.

The magnitude of the emission peaks fluctuated considerably in the presence of metal ions, as shown in FIG. 6A-6D. The fluctuation illustrates that the metal ions affect the fluorescence emission properties of the molecules. The configuration of the contour lines conveyed details regarding the emission profile and the degree of spectral overlap, as shown in FIG. 6A-6D. The introduction of $Cd^{2+}$ reduced the overall emission intensity and a minor red-shift in the emission maxima. The results indicated that $Cd^{2+}$ interacts with the fluorophore, potentially via coordination or charge transfer, thereby dimming its fluorescence. The impact of $Pb^{2+}$ on compound 1 was similar to $Cd^{2+}$ ions. The emission intensity diminished marginally, although there was no substantial alteration in the emission maximum. The introduction of $Cd^{2+}$ to compound 2 leads to an enhancement in fluorescence intensity and a minor red-shift in the emission maxima. The observations indicated a robust interaction between $Cd^{2+}$ and the fluorophore, resulting in effective aggregation-induced emission (AIE). The 2D fluorescence contour maps indicated that compounds 1 and 2 demonstrate distinctive reactions to $Cd^{2+}$ and $Pb^{2+}$ ions. As shown in FIGS. 6A-6B, the detected alterations in fluorescence intensity and spectrum location yielded significant insights into the interactions between the fluorophores and metal ions.

Figure 7:
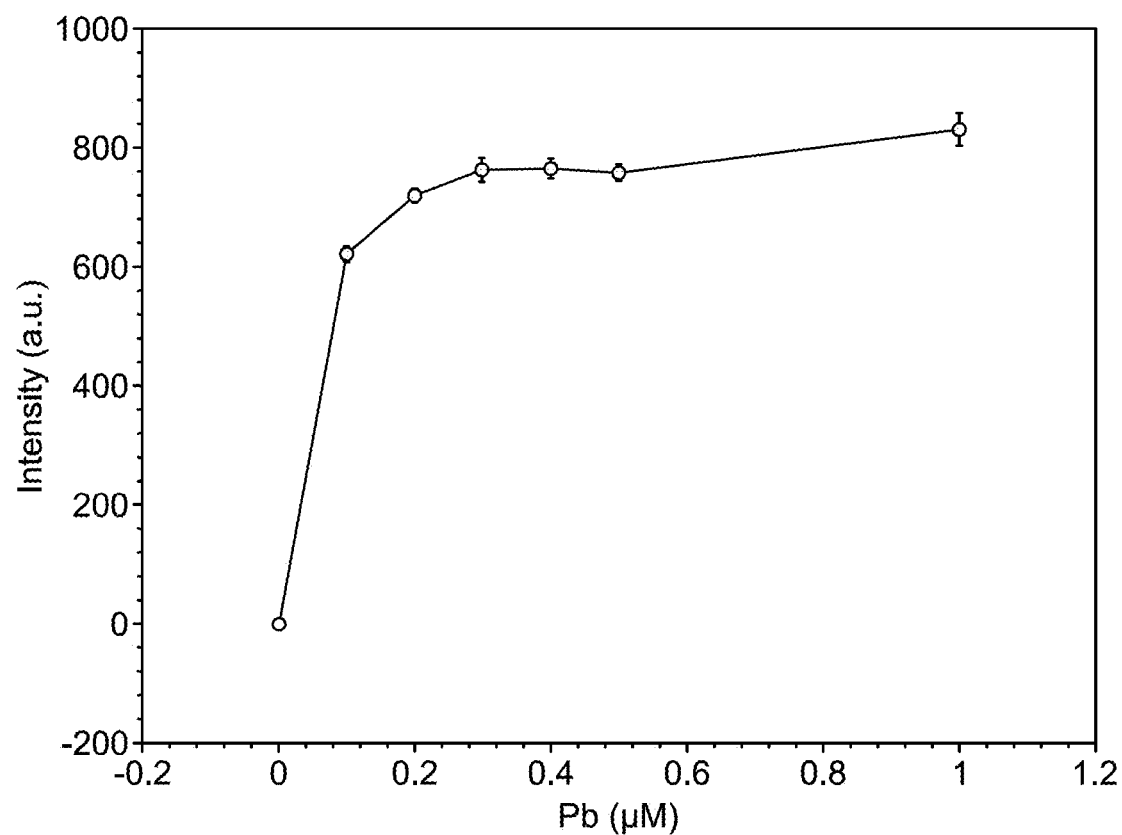
FIG. 7 is a plot showing the relationship between the fluorescence emission intensity for compound 1 and the concentration of $Pb^{2+}$ ions, according to certain embodiments.
Figure 8A:
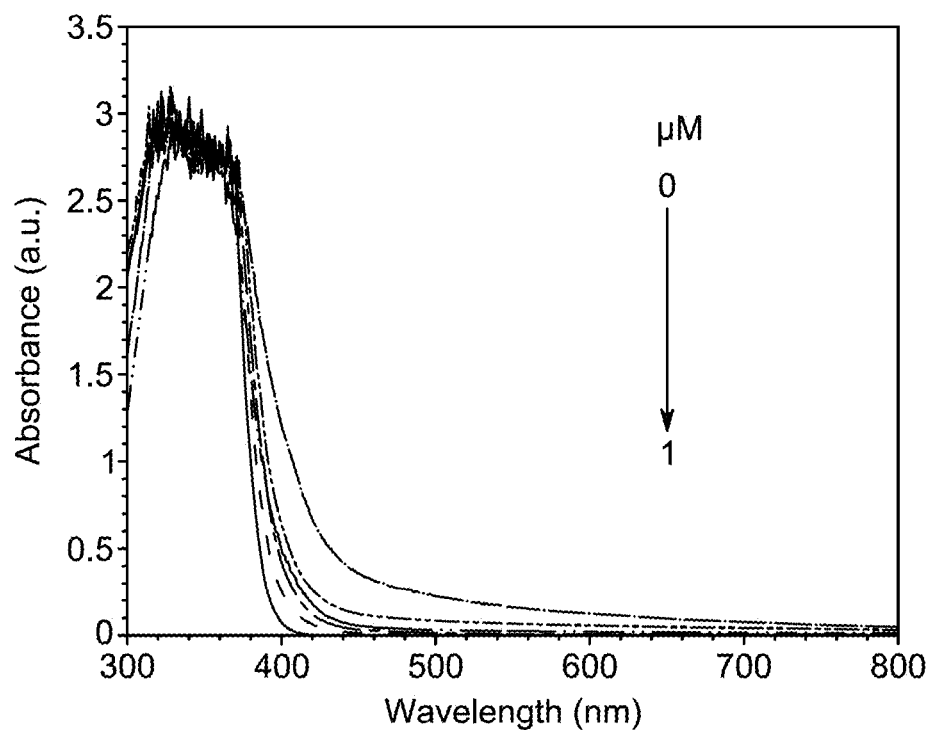
FIG. 8A shows ultraviolet-visible (UV-Vis) spectra for compound 1 in the presence of $Cd^{2+}$ ions, according to certain embodiments.
Figure 8B:
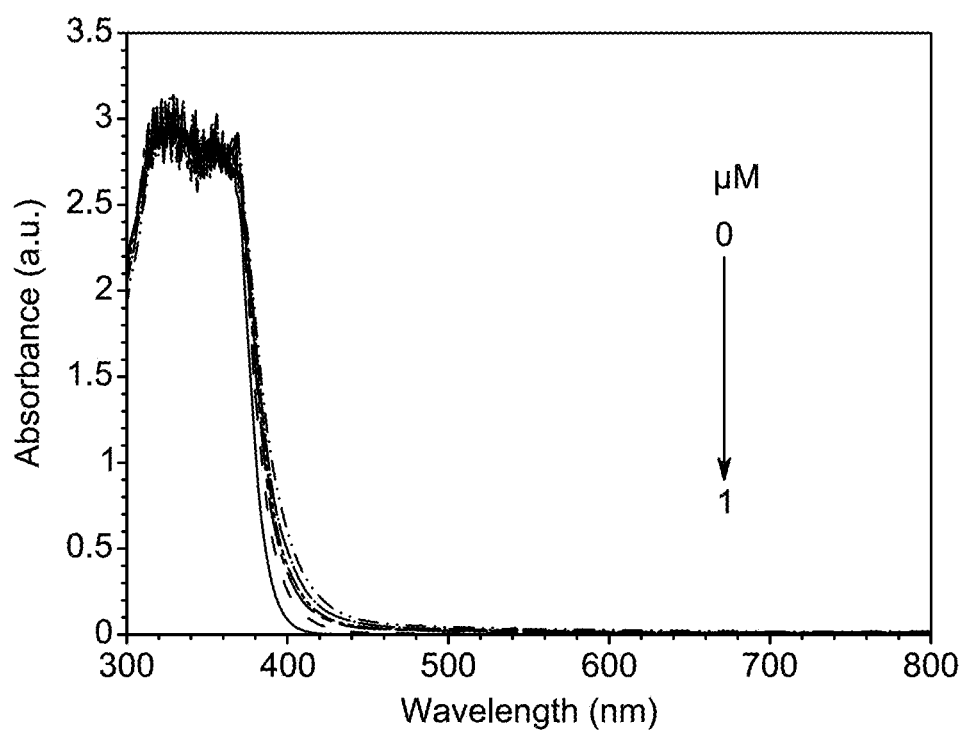
FIG. 8B shows a UV-Vis spectra for compound 1 in the presence of $Pb^{2+}$ ions, according to certain embodiments.
Figure 8C:
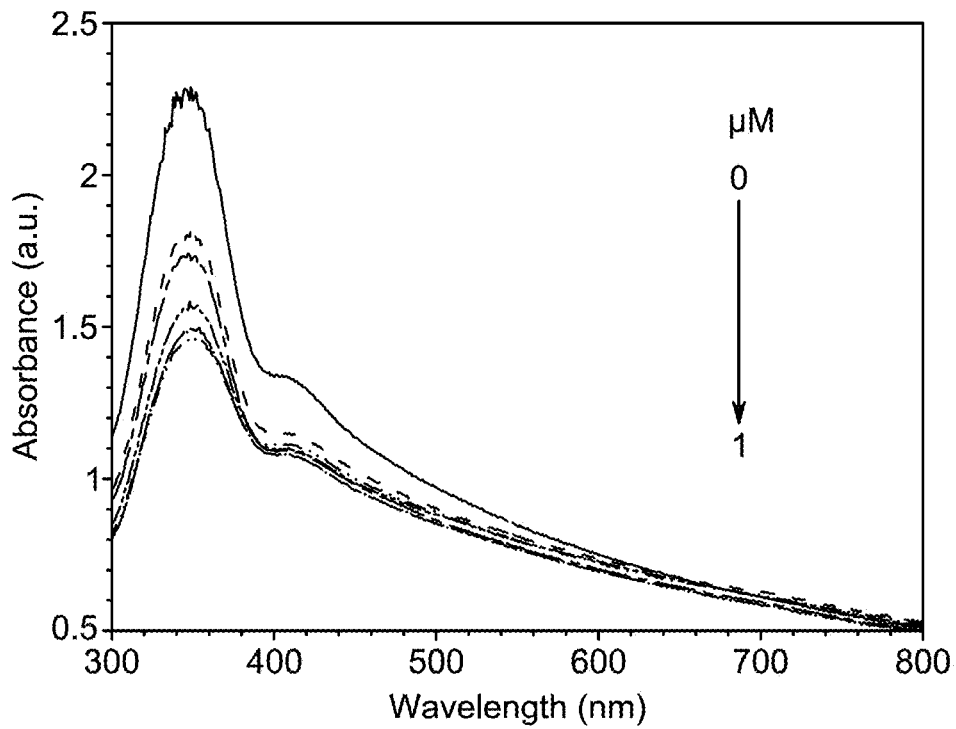
FIG. 8C shows a UV-Vis spectra for compound 2 in the presence of $Cd^{2+}$ ions, according to certain embodiments.
Figure 8D:
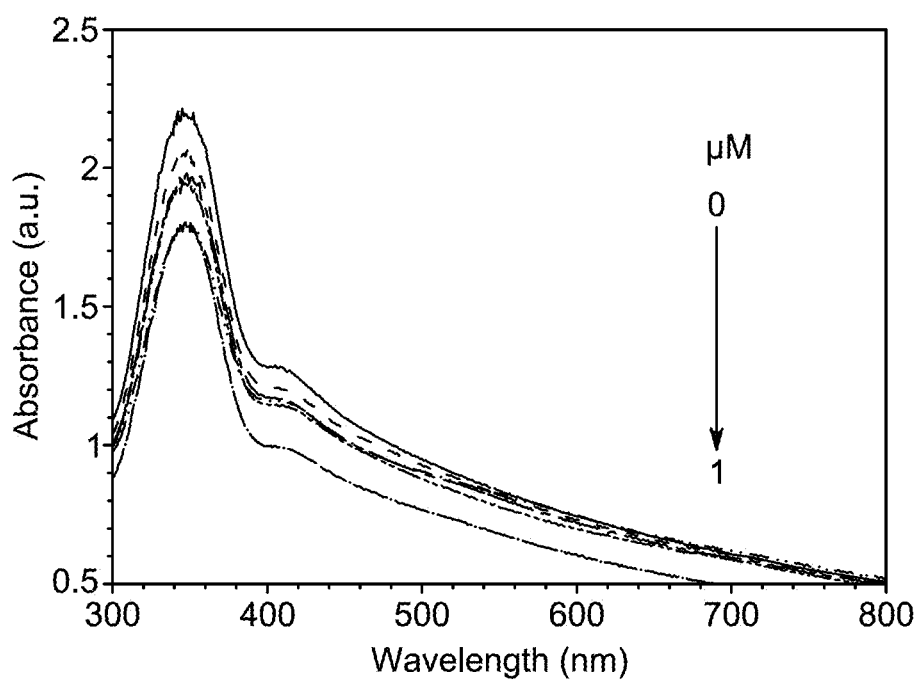
FIG. 8D shows a UV-Vis spectra for compound 2 in the presence of $Pb^{2+}$ ions, according to certain embodiments.

A graph depicting the correlation between fluorescence emission intensity and $Pb^{2+}$ ion concentration, as shown in FIG. 7. With an increase in $Pb^{2+}$ concentration, the fluorescence intensity initially ascends, peaking at approximately 0.4 µM. Beyond the approximate concentration, the emission intensity reached a steady state. Therefore, the behavior of the effect of concentration indicated that $Pb^{2+}$ ions engaged with the fluorophore, first augmenting its fluorescence. At elevated concentrations, the metal ions may inhibited fluorescence or trigger other processes that reduce the overall emission intensity, as shown in FIG. 7.

UV-Vis spectroscopy quantifies the absorption of light by a material across varying wavelengths, as shown in FIG. 8A-8D. The introduction of $Cd^{2+}$ ions resulted in a reduction of absorbance throughout the entire wavelength spectrum. The examination indicated that the metal ions engaged in the chemical structure of organic fluorophores, possibly creating complexes that reduced the quantity of free chromophores available for light absorption. Similar to $Cd^{2+}$, the addition of $Pb^{2+}$ ions resulted in a decrease in absorbance. Nonetheless, the effect was less significant, illustrating a diminished interaction between $Pb^{2+}$ and the molecule. The introduction of $Cd^{2+}$ ions showed a notable reduction in absorbance, especially in the vicinity of 400 nm. Consequently, it indicates a robust interaction between $Cd^{2+}$ and the molecule, resulting in alterations to the electronic structure or the creation of complexes. The influence of $Pb^{2+}$ ions on compound 2 was less significant than that of $Cd^{2+}$ ions. The reduction in absorbance was minimal, demonstrating a diminished interaction between $Pb^{2+}$ and the molecule, as shown in FIG. 8A-8D.

Various potential mechanisms for the observed changes include metal complexation, aggregation, and charge transfer. The metal ions may form complexes with the compounds, altering the electrical structure and absorption characteristics. The presence of metal ions may promote the aggregation of the compounds, thereby influencing the light absorption characteristics. Metal ions may transfer charge with molecules, altering the absorption spectra. The UV-Vis spectra demonstrate the interaction of compounds 1 and 2 with $Cd^{2+}$ and $Pb^{2+}$ ions. The detected alterations in absorbance indicate that the metal ions may affect the compounds' electronic configuration and aggregation state.

Figure 9A:
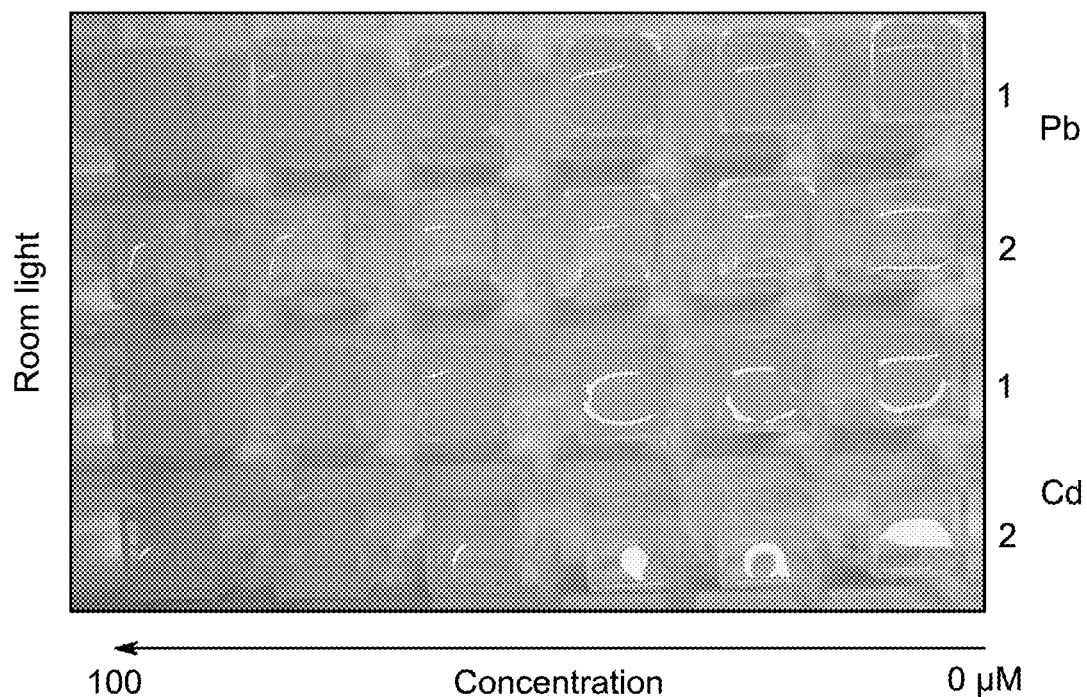
FIG. 9A is a picture captured for the solution under room light for compounds 1 and 2 with different concentrations of $Pb^{2+}$ and $Cd^{2+}$, according to certain embodiments.
Figure 9B:
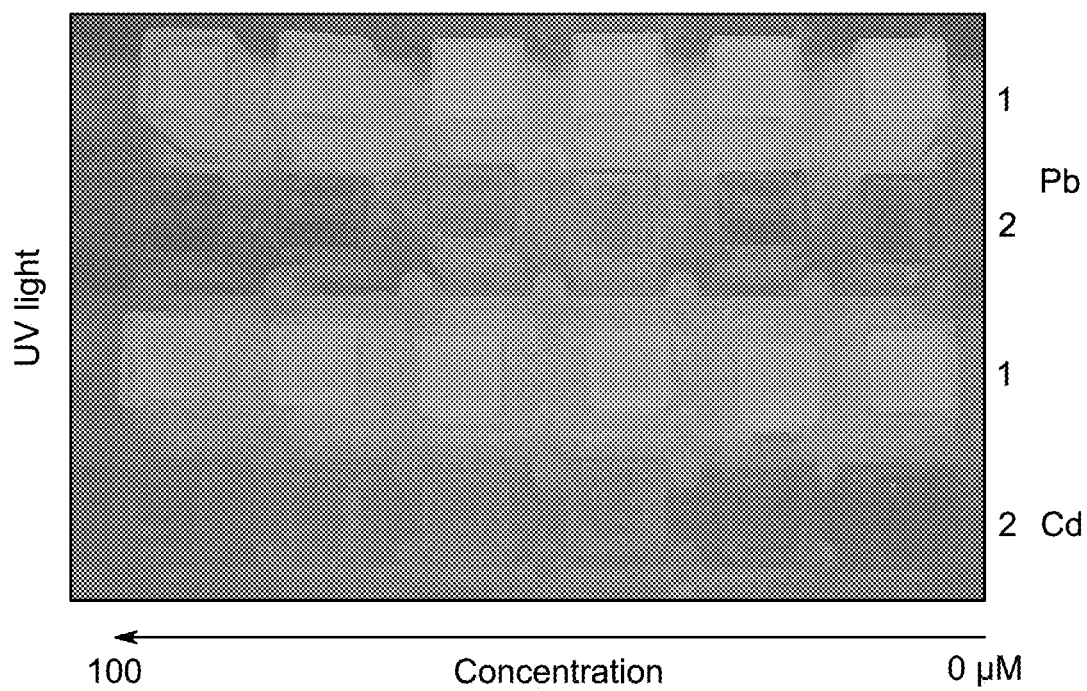
FIG. 9B is a picture captured for the solution under UV light for compounds 1 and 2 with different concentrations of $Pb^{2+}$ and $Cd^{2+}$, according to certain embodiments.

As shown in FIGS. 9A-9B, the visual reaction observations of compounds 1 and 2 to varying amounts of $Pb^{2+}$ and $Cd^{2+}$ ions under ambient and UV light conditions. Compound 1 demonstrated a distinct fluorescence response under UV light in the presence of both metal ions i.e., $Cd^{2+}$ and $Pb^{2+}$ ions, as shown in FIG. 9A-9B. The fluorescence intensity escalated with higher concentrations of metal ions, indicating that the compounds may function as fluorescent sensors for these ions. Under ambient light, the solutions appeared either colorless or slightly yellow, illustrating that the compounds exhibit minimal coloration under these conditions. The detected fluorescence amplification under UV light indicated that the metal ions interacted with the fluorophores in the compounds, resulting in alterations to the electronic structure and emission characteristics. The interaction may entail complex formation and energy transfer mechanisms. The rise in fluorescence intensity with higher metal ion concentration indicated a positive association between the degree of metal ion binding and the fluorescence response.

Figure 10:
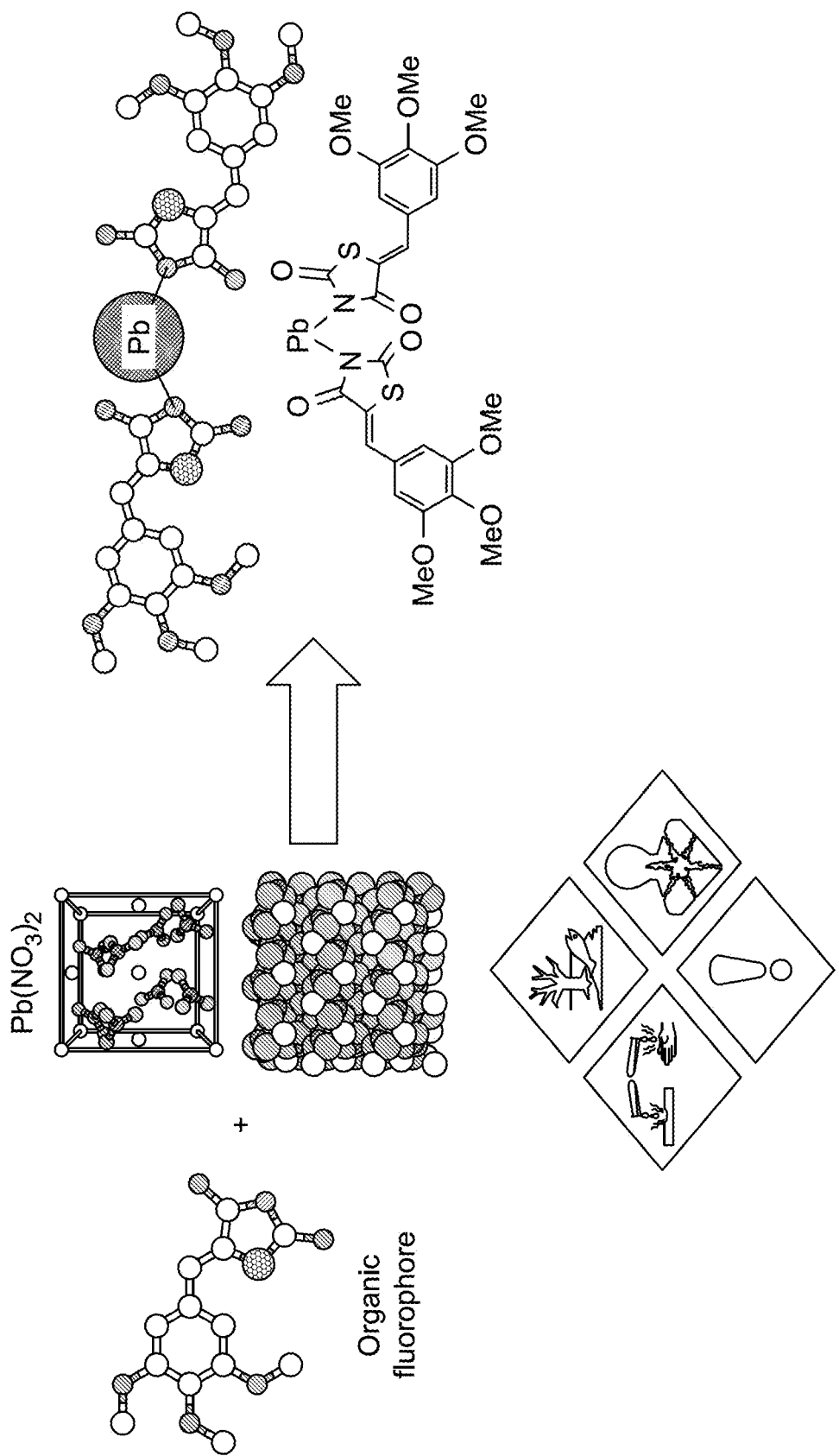
FIG. 10 is a schematic representation of the interaction between $Pb^{2+}$ and organic fluorophore, according to certain embodiments.

Based on UV-Vis spectra, compounds 1 and 2 generated metal complexes leading to static quenching via energy transfer, as shown in FIG. 10. The presence of the N—H site in the organic fluorophore enabled complexation with $Pb(NO_3)_2$. Nitrogen experienced deprotonation, forming N-which binds to $Pb^{2+}$ ions forming bis(1,3-thiazolidine-2, 4-diones) lead (II) complex, as shown in FIG. 10.

Numerous modifications and variations of the present disclosure are possible in light of the above teachings. It is, therefore, to be understood that within the scope of the appended claims, the invention may be practiced otherwise than as specifically described herein.

The invention claimed is:

1. A method of detecting a heavy metal ion in an aqueous sample, comprising:

contacting a potassium salt of 5-(3,4,5-trimethoxybenzylidene) thiazolidine-2,4-dione with the aqueous sample to form a heavy metal complex with the heavy metal ion; and measuring the fluorescence emission of the aqueous sample to detect the heavy metal complex, wherein the heavy metal ion is least one selected from the group consisting of lead, cadmium, copper, zinc, mercury, and nickel, wherein the aqueous sample has a pH of 1 to 10, and wherein the heavy metal ion is present in the aqueous sample in an amount of at least 0.1 µM.

2. The method of claim 1, further comprising:

obtaining a thiazolidine-2,4-dione by reacting chloroacetic acid with a thiourea; and condensing the thiazolidine-2,4-dione with a tri-substituted benzaldehyde in the presence of a catalyst, to obtain 5-(3,4,5-trimethoxybenzylidene) thiazolidine-2, 4-dione, then reacting the 5-(3,4,5-trimethoxybenzylidene) thiazolidine-2,4-dione with potassium hydroxide to form the potassium salt of 5-(3,4,5-trimethoxybenzylidene) thiazolidine-2,4-dione.

3. The method of claim 2, wherein obtaining the thiazolidine-2,4-dione comprises reacting chloroacetic acid with a thiourea in a molar ratio of 1:3 to 3:1.

4. The method of claim 2, wherein the condensing comprises condensing the thiazolidine-2,4-dione with the tri-substituted benzaldehyde in a molar ratio of 1:2 to 2:1.

5. The method of claim 2, wherein the catalyst comprises acetic acid and at least one amine selected from the group consisting of piperidine, 4-methylpiperidine, piperazine, pyrrolidine, and hexamethyleneimine.

6. The method of claim 2, wherein the catalyst comprises piperidine and acetic acid.

7. The method of claim 1, wherein the potassium salt of 5-(3,4,5-trimethoxybenzylidene) thiazolidine-2,4-dione has a band gap of 2 to 3.5 eV.

8. The method of claim 1, wherein the heavy metal ion is at least one selected from the group consisting of lead and cadmium, wherein the total concentration of the heavy metal ion in the aqueous sample is from 0.1 to 1 µM, and wherein the aqueous sample does not contain any organic material other than the potassium salt of 5-(3,4,5-trimethoxybenzylidene) thiazolidine-2,4-dione, and wherein the fluorescence emission is measured by irradiating the aqueous sample with UV light at a slit size of 20 nm and measuring the fluorescence emission at 350-500 nm.

9. The method of claim 1, wherein the heavy metal ion is lead and two units of the salt of 5-(3,4,5-trimethoxybenzylidene) thiazolidine-2,4-dione bind with one $Pb^{2+}$ ion.

10. The method of claim 1, wherein the potassium salt of 5-(3,4,5-trimethoxybenzylidene) thiazolidine-2,4-dione is characterized by a DRS pattern comprising a broad absorption band at 300 to 500 nm.

11. The method of claim 1, wherein a fluorescence emission of the potassium salt of 5-(3,4,5-trimethoxybenzylidene) thiazolidine-2,4-dione is 5 to 35 a.u. at a wavelength of 400 to 500 nm when 0.1 to 1 µM of lead is present in the aqueous sample.

12. The method of claim 1, wherein a fluorescence emission of the potassium salt of 5-(3,4,5-trimethoxybenzylidene) thiazolidine-2,4-dione is 20 to 35 a.u. at a wavelength of 460 to 500 nm when 0.1 to 1 µM of lead is present in the aqueous sample.

13. The method of claim 1, wherein the potassium salt of 5-(3,4,5-trimethoxybenzylidene) thiazolidine-2,4-dione is a direct band gap material.

14. The method of claim 1, wherein a fluorescence emission of the potassium salt of 5-(3,4,5-trimethoxybenzylidene) thiazolidine-2,4-dione potassium salt is 10 to 30 a.u. at a wavelength of 400 to 600 nm at a pH of 1 to 3.

15. The method of claim 1, wherein a fluorescence emission of the potassium salt of 5-(3,4,5-trimethoxybenzylidene) thiazolidine-2,4-dione is 5 to 30 a.u. at a wavelength of 400 to 600 nm when 0.1 to 1 µM of cadmium is present in the aqueous sample.

16. The method of claim 1, wherein a fluorescence emission of the potassium salt of 5-(3,4,5-trimethoxybenzylidene) thiazolidine-2,4-dione is 15 to 30 a.u. at a wavelength of 460 to 500 nm when 0.1 to 1 µM of cadmium is present in the aqueous sample.

17. The method of claim 1, wherein the aqueous sample has a pH of 1 to 8.

18. The method of claim 1, wherein the contacting comprises contacting the potassium salt of 5-(3,4,5-trimethoxybenzylidene) thiazolidine-2,4-dione to the aqueous sample for 20 minutes.

19. The method of claim 1, wherein the aqueous sample has a pH of 1 to 3.

20. The method of claim 1, wherein the potassium salt of 5-(3,4,5-trimethoxybenzylidene) thiazolidine-2,4-dione has a melting point of 170° C. to 260° C.

* * * * *